US011978556B2

(12) United States Patent
Liu et al.

(10) Patent No.: US 11,978,556 B2
(45) Date of Patent: May 7, 2024

(54) GENE MUTATIONS ASSOCIATED WITH TANDEM DUPLICATOR PHENOTYPE

(71) Applicant: The Jackson Laboratory, Bar Harbor, ME (US)

(72) Inventors: Edison T. Liu, Bar Harbor, ME (US); Francesca Menghi, West Hartford, CT (US)

(73) Assignee: The Jackson Laboratory, Bar Harbor, ME (US)

(*) Notice: Subject to any disclaimer, the term of this patent is extended or adjusted under 35 U.S.C. 154(b) by 1349 days.

(21) Appl. No.: 16/238,764

(22) Filed: Jan. 3, 2019

(65) Prior Publication Data

US 2019/0214139 A1   Jul. 11, 2019

Related U.S. Application Data

(60) Provisional application No. 62/613,256, filed on Jan. 3, 2018.

(51) Int. Cl.
| | |
|---|---|
| *G16H 50/20* | (2018.01) |
| *G06F 17/15* | (2006.01) |
| *G16B 20/00* | (2019.01) |
| *G16B 20/10* | (2019.01) |
| *G16B 20/20* | (2019.01) |
| *G16B 40/10* | (2019.01) |
| *G16B 40/20* | (2019.01) |
| *G16H 20/00* | (2018.01) |
| *G16H 50/30* | (2018.01) |

(52) U.S. Cl.
CPC ............. *G16H 50/20* (2018.01); *G06F 17/15* (2013.01); *G16B 20/00* (2019.02); *G16B 20/10* (2019.02); *G16B 20/20* (2019.02); *G16B 40/10* (2019.02); *G16B 40/20* (2019.02); *G16H 20/00* (2018.01); *G16H 50/30* (2018.01)

(58) Field of Classification Search
CPC ........ G16H 50/20; G16H 20/00; G16H 50/30; G06F 17/15; G16B 20/00; G16B 20/10; G16B 20/20; G16B 40/10; G16B 40/20
See application file for complete search history.

(56) References Cited

U.S. PATENT DOCUMENTS

2019/0119759 A1* 4/2019 Nik-Zainal ............ G16H 50/20

OTHER PUBLICATIONS

André et al., Optimal strategies for the treatment of metastatic triple-negative breast cancer with currently approved agents. Ann Oncol. Aug. 2012;23 Suppl 6:vi46-51.
Baca et al., Punctuated evolution of prostate cancer genomes. Cell. Apr. 25, 2013;153(3):666-77. doi: 10.1016/j.cell.2013.03.021.
Barthel et al., Systematic analysis of telomere length and somatic alterations in 31 cancer types. Nat Genet. Mar. 2017;49(3):349-357. doi: 10.1038/ng.3781. Epub Jan. 30, 2017. Author manuscript.

(Continued)

*Primary Examiner* — Jesse P Frumkin
(74) *Attorney, Agent, or Firm* — Wolf, Greenfield & Sacks, P.C.

(57) ABSTRACT

Provided herein, in some embodiments, are methods for classifying the tandem duplicator phenotype of a tumor into one of at least six TDP subtypes based on the length distribution of tandem duplications (TDs) in the genome of the tumor sample.

4 Claims, 20 Drawing Sheets

(56) References Cited

OTHER PUBLICATIONS

Cancer Genome Atlas Research Network et al., Integrated genomic characterization of endometrial carcinoma. Nature. May 2, 2013;497(7447):67-73. doi: 10.1038/nature12113. Erratum in: Nature. Aug. 8, 2013;500(7461):242.
Chiang et al., SpeedSeq: ultra-fast personal genome analysis and interpretation. Nat Methods. Oct. 2015;12(10):966-8. doi: 10.1038/nmeth.3505. Epub Aug. 10, 2015. Author manuscript.
Clancy et al., DNA deletion and duplication and the associated genetic disorders. Nature Education. 2008;1(1):23.
Cleere, Triple-negative breast cancer: a clinical update. Community Oncology. 2010;7(5):203-2011.
Costantino et al., Break-induced replication repair of damaged forks induces genomic duplications in human cells. Science. Jan. 3, 2014;343(6166):88-91. doi: 10.1126/science.1243211. Epub Dec. 5, 2013. Author manuscript.
Davoli et al., Cumulative haploinsufficiency and triplosensitivity drive aneuploidy patterns and shape the cancer genome. Cell. Nov. 7, 2013;155(4):948-62. doi: 10.1016/j.cell.2013.10.011. Epub Oct. 31, 2013.
Desmedt et al., Uncovering the genomic heterogeneity of multifocal breast cancer. J Pathol. Aug. 2015;236(4):457-66. doi: 10.1002/path.4540. Epub May 7, 2015.
Etemadmoghadam et al., Synthetic lethality between CCNE1 amplification and loss of BRCA1. Proc Natl Acad Sci U S A. Nov. 26, 2013;110(48):19489-94. doi: 10.1073/pnas.1314302110. Epub Nov. 11, 2013.
Glodzik et al., A somatic-mutational process recurrently duplicates germline susceptibility loci and tissue-specific super-enhancers in breast cancers. Nat Genet. Mar. 2017;49(3):341-348. doi: 10.1038/ng.3771. Epub Jan. 23, 2017. Author manuscript.
Hnisz et al., Super-enhancers in the control of cell identity and disease. Cell. Nov. 7, 2013;155(4):934-47. doi: 10.1016/j.cell.2013.09.053. Epub Oct. 10, 2013.
Inaki et al., Systems consequences of amplicon formation in human breast cancer. Genome Res. Oct. 2014;24(10):1559-71. doi: 10.1101/gr.164871.113. Epub Sep. 3, 2014.
Jonkers et al., Synergistic tumor suppressor activity of BRCA2 and p53 in a conditional mouse model for breast cancer. Nat Genet. Dec. 2001;29(4):418-25.
Liu et all, Somatic loss of BRCA1 and p53 in mice induces mammary tumors with features of human BRCA1-mutated basal-like breast cancer. Proc Natl Acad Sci U S A. Jul. 17, 2007;104(29):12111-6. Epub Jul. 11, 2007.
McBride et al., Tandem duplication of chromosomal segments is common in ovarian and breast cancer genomes. J Pathol. Aug. 2012;227(4):446-55. doi: 10.1002/path.4042. Epub Jul. 2, 2012.
Mendes-Pereira et al., Synthetic lethal targeting of PTEN mutant cells with PARP inhibitors. EMBO Mol Med. Sep. 2009;1(6-7):315-22. doi: 10.1002/emmm.200900041.
Menghi et al., Reply to Watkins et al.: Whole-genome sequencing-based identification of diverse tandem duplicator phenotypes in human cancers. Proc Natl Acad Sci U S A. Sep. 6, 2016;113(36):E5259-60. doi: 10.1073/pnas.1610624113. Epub Aug. 19, 2016.
Menghi et al., The tandem duplicator phenotype as a distinct genomic configuration in cancer. Proc Natl Acad Sci U S A. Apr. 26, 2016;113(17):E2373-82. doi: 10.1073/pnas.1520010113. Epub Apr. 7, 2016.
Menghi et al., The Tandem Duplicator Phenotype Is a Prevalent Genome-Wide Cancer Configuration Driven by Distinct Gene Mutations. Cancer Cell. Aug. 13, 2018;34(2):197-210.e5. doi: 10.1016/j.ccell.2018.06.008. Epub Jul. 12, 2018.
Menghi, The tandem duplicator phenotype as a distinct genomic configuration in cancer. Human Genome Meeting Feb. 28, 2016. Human Genomics. Abstract 015. 2016; 10(S1):6-7.
Natrajan et al., A whole-genome massively parallel sequencing analysis of BRCA1 mutant oestrogen receptor-negative and -positive breast cancers. J Pathol. May 2012;227(1):29-41. doi: 10.1002/path.4003. Epub Feb. 23, 2012. Author manuscript.
Ng et al., The role of tandem duplicator phenotype in tumour evolution in high-grade serous ovarian cancer. J Pathol. Apr. 2012;226(5):703-12. doi: 10.1002/path.3980. Epub Feb. 9, 2012.
Nik-Zainal et al., Landscape of somatic mutations in 560 breast cancer whole-genome sequences. Nature. Jun. 2, 2016;534(7605):47-54. doi: 10.1038/nature17676. Epub May 2, 2016. Author manuscript.
Nik-Zainal et al., Mutational processes molding the genomes of 21 breast cancers. Cell. May 25, 2012;149(5):979-93. doi: 10.1016/j.cell.2012.04.024. Epub May 17, 2012.
Popova et al., Ovarian Cancers Harboring Inactivating Mutations in CDK12 Display a Distinct Genomic Instability Pattern Characterized by Large Tandem Duplications. Cancer Res. Apr. 1, 2016;76(7):1882-91. doi: 10.1158/0008-5472.CAN-15-2128. Epub Jan. 19, 2016.
Stefansson et al., BRCA1 epigenetic inactivation predicts sensitivity to platinum-based chemotherapy in breast and ovarian cancer. Epigenetics. Nov. 2012;7(11):1225-9. doi: 10.4161/epi.22561. Epub Oct. 15, 2012.
Tang et al., CTCF-Mediated Human 3D Genome Architecture Reveals Chromatin Topology for Transcription. Cell. Dec. 17, 2015;163(7):1611-27. doi: 10.1016/j.cell.2015.11.024. Epub Dec. 10, 2015.
Wahba et al., Current approaches in treatment of triple-negative breast cancer. Cancer Biol Med. Jun. 2015;12(2):106-16. doi: 10.7497/j.issn.2095-3941.2015.0030.
Wallace et al., Comparative oncogenomics implicates the neurofibromin 1 gene (NF1) as a breast cancer driver. Genetics. Oct. 2012; 192(2):385-396. doi: 10.1534/genetics.112.142802.
Willis et al., Mechanism of tandem duplication formation in BRCA1-mutant cells. Nature. Nov. 30, 2017;551(7682):590-595. doi: 10.1038/nature24477. Epub Nov. 22, 2017. Author manuscript.
Yang et al., Diverse mechanisms of somatic structural variations in human cancer genomes. Cell. May 9, 2013;153(4):919-29. doi: 10.1016/j.cell.2013.04.010.

* cited by examiner

| K14cre; Trp53^F/F (KP) | | K14cre; Trp53^F/F Brca1^F/F (KB1P) | | K14cre; Trp53^F/F Brca2^F/F (KB2P) | | K14cre; Trp53^F/F Brca1^F/F; Brca2^F/F (KB1B2P) | | WAPcre; Trp53^F/F (WP) | | WAPcre; Trp53^F/F Brca1^F/F (WB1P) | |
|---|---|---|---|---|---|---|---|---|---|---|---|
| T | B1 B2 | T | B1 B2 | T | B1 B2 | T | B1 B2 | T | B1 B2 | T | B1 B2 |
| Δ/Δ | WT WT | Δ/Δ | Δ/Δ WT | Δ/Δ | WT Δ/Δ | Δ/Δ | Δ/Δ Δ/Δ | Δ/Δ | WT WT | Δ/Δ | Δ/Δ WT |
| Non TDP | | TDP group 1 | | Non TDP | | TDP group 1 | | Non TDP | | TDP group 1 | |
| Δ/Δ | WT WT | Δ/Δ | Δ/Δ WT | Δ/Δ | WT Δ/Δ | Δ/Δ | F/F Δ/Δ | Δ/Δ | WT WT | Δ/Δ | Δ/Δ WT |
| Non TDP | | TDP group 1 | | Non TDP | | Non TDP | | Non TDP | | TDP group 1 | |
| Δ/Δ | WT WT | Δ/Δ | Δ/Δ WT | Δ/Δ | WT Δ/Δ | Δ/Δ | Δ/F Δ/Δ | Δ/Δ | WT WT | Δ/Δ | Δ/Δ WT |
| Non TDP | | Non TDP w/ class 1 TDs | | Non TDP | | Non TDP | | Non TDP | | TDP group 1 | |

FIG. 2C

GENE MUTATIONS ASSOCIATED WITH TANDEM DUPLICATOR PHENOTYPE

RELATED APPLICATION

This application claims the benefit under 35 U.S.C. § 119(e) of U.S. provisional application No. 62/613,256, filed Jan. 3, 2018, which is incorporated by reference herein in its entirety.

GOVERNMENT LICENSE RIGHTS

This invention was made with government support under Grant No. P30CA034196 awarded by National Institutes of Health and Grant No. W81XWH-17-1-0005 awarded by Department of Defense. The government has certain rights in the invention.

BACKGROUND

Whole-genome sequencing (WGS) of large numbers of human cancers has revealed recurrent patterns of highly complex genomic rearrangements, such as chromothripsis and chromoplexy (Baca et al., 2013; Stephens et al., 2011). Recently, three groups have described an enrichment of head-to-tail somatic segmental tandem duplications (TDs) primarily associated with breast and ovarian cancers, which is commonly referred to as the tandem duplicator phenotype (TDP) (Glodzik et al., 2017; Menghi et al., 2016; Menghi and Liu, 2016; Nik-Zainal et al., 2016; Popova et al., 2016). These early reports have shown a statistical association between the TDP and loss of BRCA1 in breast cancers (Menghi and Liu, 2016; Nik-Zainal et al., 2016), loss of TP53 and overexpression of certain cell cycle and DNA replication genes primarily in breast and ovarian cancers (Menghi et al., 2016), and mutations of the CDK12 gene in a small subgroup of ovarian cancers (Popova et al., 2016). These analyses also noted that, within the TDP cancer genomes, tandem duplication span sizes are clustered around specific lengths, which can be used to classify distinct genomic subtypes of TDP. TDP tumors can be separated into at least two major subgroups: TDP group 1 tumors are BRCA1-deficient and feature short-span TDs (~10 kb), whereas TDP group 2 tumors are BRCA1 wild-type and feature medium-span TDs (~50-600 kb) (Menghi et al., 2016; Menghi and Liu, 2016). Similarly, there are two TD-based rearrangement signatures (RS), RS1 and RS3, characterized by TDs of distinct sizes: >100 kb (RS1) and <10 kb (RS3), with RS3 but not RS1 strongly correlating with loss of BRCA1 (Nik-Zainal et al., 2016). There is also a "TD plus" phenotype in some ovarian cancers featuring a large number of somatic TDs with span distribution modes at 300 kb and 3 Mb associated with disruptive CDK12 mutations (Popova et al., 2016).

SUMMARY

The tandem duplicator phenotype (TDP) is a genome-wide instability configuration primarily observed in breast, ovarian, and endometrial carcinomas. The present disclosure provides data from a meta-analysis of cancer genomes representing a variety of tumor types, used to identify the genetic drivers that converge on creating the TDP and to define the structural impact of TDs on the cancer genome. TDP tumors were stratified by classifying their tandem duplications (TDs) into three span intervals, with modal values of 11 kb, 231 kb, and 1.7 Mb, respectively. TDPs with 11 kb TDs feature loss of TP53 and BRCA1. TDPs with 231 kb and 1.7 Mb TDs associate with CCNE1 pathway activation and CDK12 disruptions, respectively. The data herein demonstrate that p53 and BRCA1 conjoint abrogation drives TDP induction by generating short-span TDP mammary tumors in genetically modified mice lacking them. Lastly, the data show how TDs in TDP tumors disrupt heterogeneous combinations of tumor suppressors and chromatin topologically associating domains while duplicating oncogenes (e.g., p53, Ableson kinase, and/or Raf kinase) and super-enhancers (groups of enhancers in close genomic proximity with unusually high levels of transcription of downstream genes, such as Oct-4, Sox2, Nanog, Klf4, and Esrrb).

The present disclosure, in some aspects, provides methods for assigning a tumor sample from a subject to one of at least six TDP subtypes based on the length distribution of tandem duplications (TDs) in the genome of the tumor sample. The length distribution of TDs is obtained by plotting the length of the TDs in a tumor sample against the number of TDs in the tumor sample. In some embodiments, the methods comprise (a) calculating a TDP score for a genome of a tumor sample obtained from a subject, (b) measuring a length distribution of tandem duplications in the tumor sample if the TDP score is above or below a threshold value, and (c) assigning to the tumor sample one of at least six TDP subtypes based on the length distribution of the tandem duplications.

In some embodiments, the TDP score of step (a) is calculated based on number and genomic location of somatic tandem duplications in the genome of the tumor sample. In some embodiments, the TDP score of step (a) is calculated using the following equation:

$$TDP\ score = -\frac{\sum_i i|Obs_i - Exp_i|}{TD} + k$$

wherein tandem duplication (TD) is the total number of tandem duplications in the tumor sample, $Obs_i$ is the observed number of tandem duplications for each chromosome i in the genome, $Exp_i$ is the expected number of tandem duplications for each chromosome i in the genome, and k is 0.71.

In some embodiments, step (b) comprises measuring the length distribution of tandem duplications in the tumor sample if the TDP score is above a threshold value.

In some embodiments, the threshold value is zero (0).

In some embodiments, the at least six TDP subtypes are selected from the group consisting of: Group 1 TDP subtype, Group 2 TDP subtype, Group 3 TDP subtype, Group 1/2mix TDP subtype, Group 1/3mix TDP subtype, and Group 2/3mix TDP subtype.

In some embodiments, the Group 1 TDP subtype is assigned to a tumor sample that comprises tandem duplications having a length of about 11 kb (e.g., 11 kb), the Group 2 TDP subtype is assigned to a tumor sample that comprises tandem duplications having a length of about 231 kb (e.g., 231 kb), the Group 3 TDP subtype is assigned to a tumor sample that comprises tandem duplications having a length of about 1.7 Mb (e.g., 1.7 Mb), the Group 1/2mix TDP subtype is assigned to a tumor sample that comprises tandem duplications having a length of about 11 kb (e.g., 11 kb) and tandem duplications having a length of about 231 kb (e.g., 231 kb), the Group 1/3mix TDP subtype is assigned to a tumor sample that comprises tandem duplications having a length of about 11 kb (e.g., 11 kb) and tandem duplications having a length of about 1.7 Mb (e.g., 1.7 Mb), and the Group 2/3mix TDP subtype is assigned to a tumor sample that comprises tandem duplications having a length of about 231 kb (e.g., 231 kb) and tandem duplications having a length of about 1.7 Mb (e.g., 1.7 Mb).

In some embodiments, the methods further comprise identifying the subject as a candidate for a therapy based on the TDP subtype of the tumor sample.

In some embodiments, the methods further comprise administering to the subject the therapy.

In some embodiments, the tumor sample is assigned a Group 1 TDP subtype, a Group 1/2mix TDP subtype, or a Group 1/3mix TDP subtype, and the method further comprises identifying the subject as a candidate for a therapy that targets tumors comprising tandem duplications in PTEN, RB1, and/or NF1. In some embodiments, the methods further comprise administering to the subject the therapy that targets tumors comprising tandem duplications in PTEN, RB1, and/or NF1. In some embodiments, the therapy modulates BRCA1 and/or p53 activity. In some embodiments, the therapy increases BRCA1 and/or p53 activity.

In some embodiments, the tumor sample is assigned a Group 2 TDP subtype, a Group 3 TDP subtype, or a Group 2/3mix TDP subtype, and the method further comprises identifying the subject as a candidate for a therapy that targets tumors comprising tandem duplications in ERRB2, MYC1, ESR1, MDM2 and/or lncRNA MALAT1. In some embodiments, the methods further comprise administering to the subject the therapy that targets tumors comprising tandem duplications in ERRB2, MYC1, ESR1, MDM2 and/or lncRNA MALAT1. In some embodiments, the therapy modulates CCNE1 activity, FBXW7 activity, CDK12 activity, and/or p53 activity. In some embodiments, the therapy decreases CCNE1 activity. In some embodiments, the therapy increases FBXW7 activity. In some embodiments, the therapy decreases CDK12 activity. In some embodiments, the therapy increases p53 activity.

Additional embodiments of the present disclosure are described in Menghi F. et al., 2018, *Cancer Cell* 34, 197-210, and Menghi F. et al. 2016, *PNAS* 113(17), E2373-E2382, the entirety of both of which, including all supplemental material, is incorporated herein by reference.

BRIEF DESCRIPTION OF THE DRAWINGS

(FIG. 1A) Representative TD span size distribution profiles for the six identified TDP subgroups. Individual distribution peaks are plotted with circles. Vertical lines indicate the three modal span sizes at 11 kb, 231 kb, and 1.7 Mb. (FIG. 1B) Schematic overview of the TDP group classification approach. (FIG. 1C) Left: convergence between the TDP group 2/3mix profile and tumors classified as CDK12 TD-plus by Popova et al. (2016). Right: overlap between the TDP classification and RS3- and RS1-positive tumors as defined by Nik-Zainal et al. (2012). Numbers in parenthesis indicate the sample size for each tumor subclass. (FIG. 1D) Bar chart of the relative proportion of each TDP group across the 31 tumor types examined. *Binomial test statistics was applied to identify tumor types that are overall enriched or depleted for the TDP.

FIGS. 2A-2D. Conjoint Abrogation of BRCA1 and TP53 Results in TDP with Class 1 TDs. (FIG. 2A) Percentage of tumor samples with abrogation of the BRCA1 gene. Only tumor type/TDP group combinations comprising at least eight samples were analyzed. NA, data not available; non, non-TDP; g1, g1/2mix, g1/3mix, g2, g3, g2/3mix: TDP groups 1, 1/2mix, 1/3mix, 2, 3, and 2/3mix; OTHER: all tumor types except triple negative breast cancer (TNBC), ovarian cancer (OV), and uterine corpus endometrial cancer (UCEC). (FIG. 2B) Percentage of tumor samples with TP53 somatic mutations. Annotations as in (FIG. 2A). Number of samples for each tumor type/TDP group combination do not necessarily match those reported in (FIG. 2A) because of missing values. (FIG. 2C) TDP classification for mouse breast cancers with somatic loss of Trp53 and/or Brca1/2. T, Trp53; B1, Brca1; B2, Brca2. (FIG. 2D) Span sizes of TDs found in Trp53/Brca1 null tumors (left) and in Brca1-proficient tumors (right). *p<0.001, p<0.01, *p<0.05, by (1) generalized linear mixed model with tumor type as the random effect or (2) Fisher's exact test.

(FIG. 3A) Percentage of tumor samples with damaging mutations affecting CDK12. (FIG. 3B) Percentage of tumor samples showing CCNE1 pathway activation (FBXW7 somatic mutation or CCNE1 amplification). Annotations as in FIG. 2A. ***p<0.001, *p<0.05, by (1) generalized linear mixed model with tumor type as the random effect or (2) Fisher's exact test.

(FIG. 4A) Genomic distribution of hotspots for TD breakpoints found in non-TDP tumors. (FIG. 4B) Genomic distribution of hotspots for TD breakpoints found in TDP tumors. Top three panels: genomic hotspots for class 1, class 2, and class 3 TDs. Lower panel: recurrent genomic hotspots across different TD classes. Known oncogenes and TSGs are flagged, respectively.

(FIG. 5A) Number of gene double and single transections and gene duplications caused by TDs of different span sizes. (FIG. 5B) Number of TD-mediated gene double transections in TDP tumors with class 1 TDs (TDP groups 1, 1/2mix, and 1/3mix) compared with the other TDP tumors. Boxes span the interquartile range, with the median values marked by a horizontal line inside the box. Whiskers extend to 1.5 times the interquartile range from each box. p values by Mann-Whitney U test. (FIG. 5C) Number of TD-mediated gene duplications in TDP tumors with a prevalence of class 2 and class 3 TDs (TDP groups 2, 3, and 2/3mix) compared with the other TDP tumors. Boxes span the interquartile range, with the median values marked by a horizontal line inside the box. Whiskers extend to 1.5 times the interquartile range from each box. p values by Mann-Whitney U test. (FIG. 5D) TSG and oncogene enrichment across sets of genes recurrently impacted by TDs via single or double transection or duplication. *p<0.001, p<0.01, *p<0.05, by Fisher's exact test. (FIG. 5E) Recurrently TD-impacted genes by TD class and type of TD-mediated effect. Top: number of genes recurrently impacted by TDs in TDP tumors. Bottom: prevalence of TD-mediated gene disruptions: x-axis, genomic location; y-axis, cumulative fraction of affected TDP tumors across the different tumor types examined. Selected genes are flagged for easy of reference. (FIG. 5F) High density of class 1 TDs at the PTEN locus in both the TNBC and OV datasets. (FIG. 5G) Percentage of TDP tumors affected by significantly recurrent class 1 TD-mediated double transection events across the TNBC and OV datasets.

(FIG. 6A) Percentage of class 1, 2, and 3 TDs involved in the duplication of disease-associated SNPs and tissue-specific super-enhancers (observed versus expected) in the TNBC and OV datasets. (FIG. 6B) Percentage of class 1, 2, and 3 TDs participating in TAD boundary duplication (observed versus expected) in the TNBC and OV datasets. p values by chi-square test.

(FIG. 7A) Number of known cancer genes per genome that are duplicated or disrupted as a result of specific TDP configurations. (FIG. 7B) Boxplot summary of the data presented in (FIG. 7A). Boxes span the interquartile range, with the median values marked by a horizontal line inside the box. Whiskers extend to 1.5 times the interquartile range from each box, and outliers are drawn as individual points extending past the whiskers

DETAILED DESCRIPTION

Figure 1A:
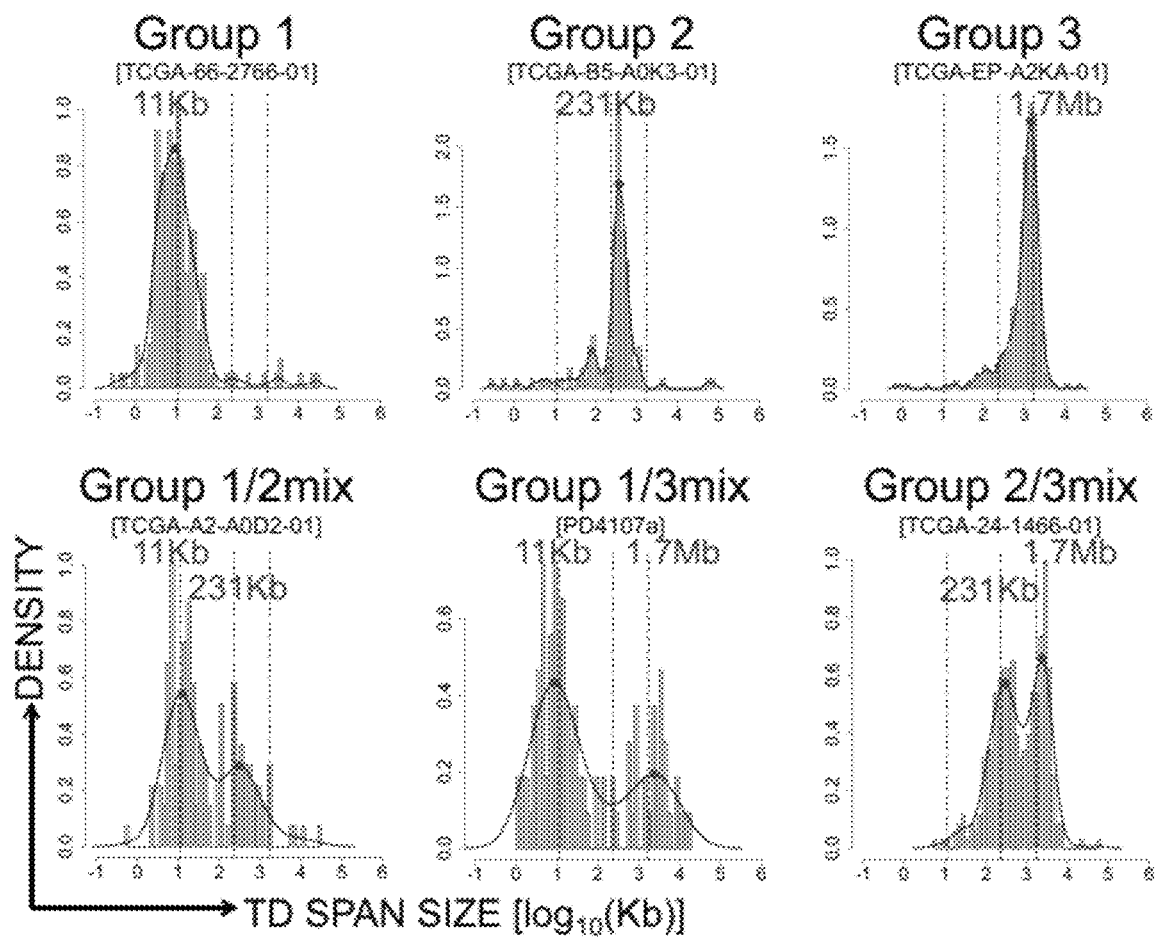
FIGS. 1A-1D. Classification of TDP Genomes into Six Distinct Subgroups.

The present disclosure provides a detailed analysis of one cancer chromotype, the TDP, by devising a quantitative scoring system to better define TDP taxonomy. The data show that TDPs can be classified by the predominant span size of their TDs: 11 kb (i.e., class 1), 231 kb (i.e., class 2), and 1.7 Mb (i.e., class 3). This sub-classification was used to identify the primary drivers of genome-wide TD formation. Of all TDP tumors, those characterized by class 1 TDs, alone (i.e., TDP group 1) or in combination with other TD span sizes (i.e., TDP groups 1/2mix and 1/3mix) were significantly enriched for the conjoint loss of BRCA1 and p53. The data herein proved the genesis of the TDP group 1 configuration in murine models of mammary cancers driven by the homozygous deletion of Trp53 and Brca1, suggesting that perturbation of BRCA1 has universal genome-wide effects distinct from BRCA2.

In support of this model, we have recently defined the mechanism of TD formation in murine embryonic stem cell (ESC) cultures, where TDs form at sites of replication fork stalling in Brca1-depleted cells by a mechanism that entails re-replication of kilobases-long tracts of chromosomal DNA adjacent to the site of fork stalling (Willis et al., 2017). This effect was also specific to BRCA1 loss and was not a feature of BRCA2 loss. The striking similarities between the genetic control of TD formation in this model and the induction of TDP group 1 tumors strongly suggest that class 1 TDs in cancer arise by similar aberrant re-replication at stalled forks exclusively in the presence of defective activity of the BRCA1 protein. Though Trp53 was not genetically disrupted in the ESC culture model, it is known that the p53 protein in mouse embryonic stem cells (ESCs) does not translocate to the nucleus in response to DNA damage to activate a p53-dependent response (Aladjem et al., 1998). Thus, mouse ESCs are functionally deficient in p53, closely resembling the TP53 null condition identified in TDP tumors. Precisely how loss of BRCA1 "licenses" class 1 TD formation and why BRCA2 does not is currently unknown. In this regard, although BRCA1 and BRCA2 have common roles in regulating RAD51-mediated homologous recombination (HR) and at stalled forks, BRCA1 has additional functions in double-strand break (DSB) repair and in-stalled fork metabolism that are not shared with BRCA2 (Aladjem et al., 1998; Pathania et al., 2011; Prakash et al., 2015; Schlacher et al., 2012). The genetic origins of the BRCA1-proficient TDP subgroups (groups 2, 3, and 2/3mix), characterized by larger class 2 (~231 kb), and/or class 3 (~1.7 Mb) TDs, are more heterogeneous. By association, it was shown that activation of the CCNE1 pathway either through CCNE1 amplification or by FBXW7 mutation accounted for 40% of TDP group 2 tumors across each one of the TNBC, OV, and UCEC datasets, but only manifested in 10% of non-TDP and <3% TDP group 1 tumors. CCNE1 is known to engage cyclin-dependent kinases to regulate cell-cycle progression. Its deregulation causes replicative stress by slowing replication fork progression, reducing intracellular nucleotide pools (Bester et al., 2011), and inducing cells to enter into mitosis with short incompletely replicated genomic segments (Teixeira et al., 2015). As a model of oncogene-induced replicative stress, CCNE1 overexpression in U2OS cells induced copy-number alterations, which were predominantly segmental duplications (Costantino et al., 2014).

Somatic mutations affecting CDK12 were most prevalent in TDP group 2/3mix tumors, which comprise both class 2 and class 3 TDs, indicating a mechanism of TD formation distinct from the augmented CCNE1 function hypothesized for TDP group 2 tumors. CDK12 is an RNA polymerase II C-terminal domain kinase that transcriptionally regulates several HR genes. Defects in CDK12 are associated with the downregulation of critical regulators of genomic stability such as BRCA1, ATR, FANCI, and FANCD2 (Blazek et al., 2011; Joshi et al., 2014). That loss of CDK12 affects BRCA1 expression but generates a TDP profile that is clearly distinct from the BRCA1-dependent TDP group 1 configuration suggests that the primary action of CDK12 is likely to be different from its effects on BRCA1.

The TDP is a model for combinatorial genetics in cancer. By classifying the effect of TDs on gene bodies, the data herein shows that the TDP generates a genome-scale pro-oncogenic configuration resulting from the modulation of tens of potential oncogenic signals. These effects were mediated systematically by TDs of different span sizes, with larger TDs (class 2 and class 3, >231 kb) being mostly involved in the duplication of oncogenes and regulatory elements and TAD disruption, and shorter TDs (class 1, ~11 kb) more frequently causing TSG disruptions.

The top three genes disrupted by class 1 TDs were PTEN and RB1 in both TNBC and OV cancer types and NF1 in the OV dataset. These genes are predominantly implicated in cell survival and cell-cycle regulation through the PI3K, E2F, and RAS pathways. However, recent evidence showed a role for their products in modulating genetic instability. RB1 has been reported to be essential for DNA DSB repair by canonical non-homologous end joining, a defect invoked to explain the high incidence of genomic instability in RB1-mutant cancers (Cook et al., 2015). PTEN has been considered a major factor in genome stability through its effects on maintaining centromere stability, by controlling RAD51 expression (Shen et al., 2007), and by recruitment of RAD51 through physical association of PTEN with DNA replication forks. These studies suggest a function for PTEN with RAD51 in promoting the restart at stalled replication forks (He et al., 2015). The role of NF1 in HR-deficient tumors, although statistically observed, is less established. However, the C3HMcm4Chaos3/Chaos3 mouse model, which harbors a disruption of Mcm4 (encoding a member of the family of MCM2-7 replicative helicases), invariably results in mammary cancers with Nf1 deletions and chromosomal instability (Wallace et al., 2012). Thus, TDP groups 1, 1/2mix, and 1/3mix tumors, which originate with defects in BRCA1-mediated HR mechanisms, appear to compound the defect by accumulating downstream mutations that disable genes involved in chromosomal stability and DNA repair, in addition to cellular functions such as cell-cycle and cellular metabolism. By contrast, TDP groups 2, 2/3mix, and 3 tumors recurrently duplicate oncogenes such as MYC and ERBB2, oncogenic lncRNAs such as MALAT1, and disrupt TADs. This would suggest that, although the genomic characteristic is TD formation, the functional consequences of TD-induced abnormalities vary significantly between the TDP forms.

Taken together, the data herein suggest a mechanistic scenario for TDP induction, where specific HR defects (e.g., loss of BRCA1 or CDK12, but not of BRCA2) and excessive replicative stress (CCNE1 pathway activation) in the presence of replication fork stalling enhance TD formation. In 91% (151/166) of TDP cancers with full genomic mutational ascertainment definitively involving one of these three driver genes, concomitant mutation of TP53 were observed, implying that defective DNA damage checkpoint control facilitated tumorigenesis, TD formation, or both. Although disruptions of each of these genes have in the past been implicated in general genomic instability, these findings reveal that these oncogenic drivers induce a much more specific pattern of structural rearrangements (i.e., the TDP) than was previously suspected.

The analysis of the gene disruptions as a consequence of TDP raises other therapeutic possibilities. Potentially disruptive double transections of PTEN were found in 16% of TNBCs with class 1 TDs. PTEN knockout cells were preferentially sensitive to poly (ADP-ribose) polymerase (PARP) inhibitors in a synthetic lethal screen (Mendes-Pereira et al., 2009) suggesting that TDPs with PTEN disruptions may have greater deficiencies in DNA repair and may be more sensitive to a range of agents that include cisplatin and PARP inhibitors. In fact, the number of known cancer genes affected by TDs ranged from an average of ~4 (in TDP group 1) to ~60 (in TDP group 2/3mix), suggesting that the TDP is a state where the mutational combinatorics can generate a range of potential therapeutic modifiers, some of which may be exploited to enhance treatment efficacy.

The results herein provide a detailed view of a specific chromosomal configuration in cancer characterized by genomically distributed TDs that unifies a number of reports focused on individual cancer types. The data show that conjoint BRCA1 and TP53 mutations are important to forming a precise TDP state that features short-span TDs. Additional studies should further delineate the mechanisms of the other forms of TDP formation, and answer why their associated TDs are restricted to specific size ranges.

Thus, provided herein, in some aspects, are methods of assigning a tumor sample to a TDP subtype based on the length distribution of tandem duplications in the tumor sample. These TDP subtypes may be used to guide particular therapies.

Tandem Duplications

A tandem duplication (TD) is an insertion of an extra copy of a DNA sequence into a location in the genome adjacent to where the DNA sequence is typically found (Clancy, et al., 2008, DNA Deletion and duplication and the associated genetic disorders, *Nature Education*, 1(1): 23). Insertion of the extra copy of the DNA sequence in a TD results in disruptions in the genome. A TD may involve an entire single gene, entire multiple genes, a fraction of a single gene, fractions of multiple genes, or any combination thereof.

Tandem duplications (TDs) are identified in a test tumor sample by comparing the genome sequences of somatic cells in the test tumor sample against a catalog of known somatic genome sequences (e.g., hg19 human reference genome, WGS, TGCA). Aligning the test tumor sample sequences to the catalog of known sequences allows detection of breakpoints in the test tumor sample (e.g., breakpoint analysis). Breakpoints are regions on a chromosome that are broken and then rejoined, creating a new genomic sequence at the breakpoint site. These breakpoints are classified into one of four basic genomic rearrangements: TD, deletion, inversion, or inter-chromosomal translocation. TDs result in two breakpoints, so TDs are measured by counting the number of nucleotides between breakpoints where a TD has occurred.

A TD can affect a gene in multiple ways. Non-limiting examples of how a TD can affect gene expression include TDs that span the entire length of a gene, resulting in gene duplication and increased expression; TDs with two breakpoints which occur in a gene and disrupt gene expression; and TDs with only one breakpoint which occurs in a gene, resulting in a gene rearrangement which does not alter gene expression.

In some embodiments, TDs identified according to the methods provided herein have a length of about 231 kb (e.g., 231 kb±10%), about 11 kb (e.g., 11 kb±10%), or about 1.7 Mb (e.g., 1.7 Mb±10%).

A tumor sample may be a single cell, a population of cells of the same type (e.g., epithelial, connective tissue, blood), or a population of cells of at least two types. A tumor may be a solid tumor, which does not have a liquid component, or a liquid tumor, which has a liquid component and a solid component. A tumor sample may be obtained from a subject having cancer. Non-limiting methods of obtaining a tumor sample include: extracting a blood sample, surgically removing a tissue sample (e.g., biopsy), or removing a tumor from a subject. In some embodiments, the subject has breast cancer (e.g., triple negative, HER2$^-$, ER$^-$, PR$^-$, medullary carcinoma, tubular carcinoma, mucinous carcinoma, ductal carcinoma in situ), ovarian cancer (e.g., epithelial, germ cell carcinoma, stromal carcinoma, small cell carcinoma), uterine cancer (e.g., cervical carcinoma, endometrial carcinoma, carcinosarcoma, uterine leiomyosarcoma, endometrial stromal sarcoma), liver cancer, leukemia, lymphoma, bone cancer, kidney cancer, prostate cancer, stomach cancer, colorectal cancer, pancreatic cancer, brain cancer, or bone cancer.

A subject refers to an organism having a tumor. In some embodiments, a subject is a human. In some embodiments, a subject is a mouse, a pig, a rat, a dog, a cat, a cow, or a non-human primate.

Tandem Duplicator Phenotype

A tandem duplicator phenotype (TDP) is an enrichment of tandem duplications throughout the genome. Tandem duplications (TDs) are an insertion of a DNA sequence into a location in the genome where the DNA sequence is not typically found. TDs may occur in any one chromosome, in any combination of chromosomes, or in all of the chromosomes in a subject.

The present disclosure provides methods comprising calculating a tandem duplicator phenotype (TDP) score for a genome of a tumor sample obtained from a subject, measuring the length distribution of TDs in the tumor sample if the TDP is above or below a threshold value, and assigning to the tumor sample one of at least six TDP subtypes based on the length distribution of the TDs.

A TDP score is calculated based on the number and genomic location of somatic TDs in the tumor sample. A somatic TD is acquired (e.g., spontaneously) by a cell other than a germ cell (i.e., sperm or eggs). Somatic TDs may occur on any or all of the 46 chromosomes present in a cell of the tumor sample. In some embodiments, somatic TDs occur on at least 1 chromosome. In some embodiments, somatic TDs occur on all 46 chromosomes. In some embodiments, somatic TDs occur on 1-40 chromosomes. In some embodiments, somatic TDs occur on 2-35 chromosomes. In some embodiments, somatic TDs occur on 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or 46 chromosomes. For example, as described herein, the presence of a large number of dispersed somatics TDs affecting virtually every chromosome is a characteristic feature of TDP cancers. The TDs may cluster at certain hotspots, given the TDP subtype, but they can be present in many different chromosomes.

Somatic TDs may be dispersed throughout the genome of a tumor sample or clustered. Clustered somatic TDs may promote the development, growth, or spread of cancer (e.g., carcinogenesis, metastasis) when they occur in genes that regulate the cell cycle, cell growth, cell division, and/or cell death. In some embodiments, somatic TDs are clustered in genes that promote cell cycle progression, cell growth, cell division, and/or cell death (e.g., proto-oncogenes). In some embodiments, somatic TDs are clustered in genes that inhibit cell cycle progression, cell growth, cell division, and/or cell death (e.g., tumor suppressor genes). In some embodiments, somatic TDs are clustered in and decrease the expression of proto-oncogenes. In some embodiments, somatic TDs are clustered in and increase the expression of proto-oncogenes. In some embodiments, somatic TDs are clustered in and decrease the expression of tumor suppressor genes. In some embodiments, somatic TDs are clustered in and increase the expression of tumor suppressor genes.

The TDP score is calculated based on the number and genomic location of somatic TDs in the genome of a tumor sample. The number of TDs are calculated as described above, and the genomic location of somatic TDs are analyzed for each chromosome by comparing the number of observed TDs and the number of expected TDs for that chromosome in the tumor sample. A tumor sample from a subject may be identified as having a TDP phenotype using the following equation:

$$TDP \text{ score} = -\frac{\sum_i i |Obs_i - Exp_i|}{TD} + k$$

wherein TD is the total number of tandem duplications in the tumor sample, as calculated above. $Obs_i$ is the observed number of TDs for each chromosome i in the genome and is obtained by separating the total number of TDs in a sample by chromosome. $Exp_i$ is the expected number of TDs for each chromosome i in the genome. The $Exp_i$ is calculated using the total number of TDs in a sample. Each chromosome, i, will have an expected number of TDs based on the length of the chromosome if the TDs in the tumor sample are perfectly evenly distributed. K is a constant that will vary based on a tumor sample and will normalize all values to a threshold for determining TDP. Tumor samples that yield TDP scores that are below this threshold will be classified as non-TDP and tumor samples that yield TDP scores that are at or above this threshold will be classified as TDP.

In a tumor sample in which the TDs are evenly distributed throughout the entire genome, the $Obs_i$ and the $Exp_i$ values are identical for each chromosome. In a tumor sample in which the TDs are not evenly distributed throughout the entire genome, the Obs value may be higher or lower than the Exp value for a given chromosome i. If the Obs value is higher than the Exp value for a chromosome, then that chromosome has more TDs than expected. If the Obs value is lower than the Exp value for a chromosome, then that chromosome has less TDs than expected. In some embodiments, tumor samples will have chromosomes that have more TDs than expected in genes that promote carcinogenesis (e.g., tumor suppressor genes, proto-oncogenes, etc). In some embodiments, tumor samples will have chromosomes that have less TDs than expected in genes that inhibit carcinogenesis (e.g., cell cycle control genes).

To obtain a k value for a tumor sample, in some embodiments, the TDP score distribution is plotted for the tumor sample. The distribution of TDP scores illustrates the number of distinct groups that the tumor sample can be separated into based on propensity to form TDs, wherein a unimodal distribution suggests 1 group (e.g., 1 non-TDP or 1 TDP), a bimodal distribution suggests 2 groups (e.g., 1 non-TDP and 1 TDP), a trimodal distribution suggests 3 groups (e.g., 1 non-TDP and 2 TDP or 2 non-TDP and 1 TDP), etc. The threshold for classifying TDP is 2 standard deviations from the middle-modal peak. For example, if the tumor sample gives a trimodal distribution, then the threshold for classifying TDP is 2 standard deviations from the second modal peak. The k value for a dataset is the absolute value of the threshold for classifying TDP.

In some embodiments, k is 0.71. In some embodiments, k is 0 to 1.0. In some embodiments, k is 0.2 to 0.8. In some embodiments, k is at least 0.1. In some embodiments, k is less than 1.0. In some embodiments, k is 0, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 0.99, or 1.0.

In some embodiments, the threshold value for calculating a TDP score is at least 0. In some embodiments, the threshold value for calculating a TDP score is between −1.0 and 1. In some embodiments, the threshold value for calculating a TDP score is between −1.0 and 0. In some embodiments, the threshold value for calculating a TDP score is between 0 and 1.0. In some embodiments, the threshold value for calculating a TDP score is −1.0, −0.9, −0.8, −0.7, −0.6, −0.5, −0.4, −0.3, −0.2, −0.1, 0, 0.1, 0.2, 0.3, 0.4, 0.5, 0.6, 0.7, 0.8, 0.9, or 1.0.

The length distribution of the TDs is measured if the TDP score of the tumor sample is above or below the threshold value. The length distribution is measured by plotting the length of the TD (in $log_{10}$ (kilobases)) versus the number of TDs and analyzing the resulting distribution for both the number of modes (e.g., peaks in the distribution), and the length of the TD than corresponds to the middle of the modes. For example, if the tumor sample gives a unimodal distribution with a peak at 250 kb, then the tumor sample has TDs with a length of about 250 kb. If the tumor sample gives a bimodal distribution with peaks at about 600 kb and 1.2 megabases (Mb), then the tumor sample has TDs with lengths of about 600 kb and 1.2 Mb.

Tandem Duplicator Phenotype Subtypes

There are at least six TDP subtypes based on the predominant length distribution of the TDs. The six TDP subtypes are Group 1 TDP subtype, Group 2 TDP subtype, Group 3 TDP subtype, Group 1/2mix TDP subtype, Group 1/3mix TDP subtype, and Group 2/3mix TDP subtype. Tumor samples with Group 1 TDPs comprise TDs that are about 11 kb. Tumors samples with Group 2 TDPs comprise TDs that are about 231 kb. Tumor samples with Group 3 TDPs comprise TDs that are about 1.7 Mb. Tumor samples with Group 1/2mix TDPs comprise TDs that are about 11 kb and about 231 kb. Tumor samples with Group 1/3mix TDPs comprise TDs that are about 11 kb and about 1.7 Mb. Tumor samples with Group 2/3mix TDPs comprise TDs that are about 231 kb and about 1.7 Mb.

In some embodiments, a tumor sample is a Group 1 TDP. In some embodiments, a tumor sample is a Group 2 TDP. In some embodiments, a tumor sample is a Group TDP. In some embodiments, a tumor sample is a Group 1/2mix TDP. In some embodiments, a tumor sample is a Group 1/3mix TDP. In some embodiments, a tumor sample is a Group 2/3mix TDP.

Group 1 TDP, Group 1/2mix TDP, and Group 1/3mix TDP Subtypes

The present disclosure provides a method for identifying the subject as a candidate for therapy based on the TDP subtype of their tumor sample. Candidate refers to a subject that is appropriate for a proposed treatment. Therapy refers to administration of an agent to selectively kill or inhibit the growth, proliferation, and division of tumor cells. Non-limiting examples of agents which can be used in methods of present disclosure include: alkylating agents, anthracyclines, taxanes, histone deacetylase inhibitors, topoisomerase inhibitors, kinase inhibitors, nucleotide analogs, retinoids, and vinca alkaloids and derivatives thereof.

In some embodiments, the method further comprises administering the therapy to the subject. Administering can be by any method known in the art. Non-limiting examples of administering include intravenous, intraarterial, inhalation, ingestion of solid, ingestion of liquid, intradermal, intranasal, intramucosal, intraocular, intracranial, or intrathecal.

The present disclosure provides a method for identifying the subject as a candidate for therapy based on the TDP subtype of the tumor sample. In some embodiments, when the tumor sample is assigned a Group 1 TDP subtype, a Group 1/2mix TDP subtype, or a Group 1/3mix TDP subtype, the method further comprises identifying a subject as a candidate for a therapy that targets tumors comprising TDs in PTEN, RB1, and/or NF1.

In some embodiments, a Group 1 TDP subtype, Group 1/2mix TDP subtype, or Group 1/3mix TDP subtype tumor sample has TDs in a PTEN gene (Gene ID: 5728). Phosphatase and tensin homolog (PTEN) is a phosphatidylinositol-3,4,5-triphosphate 3-phosphatase that negatively regulates intracellular levels of phosphatidylinositol-3,4,5-triphosphate in cells. PTEN functions as a tumor suppressor protein by negatively regulating the AKT/PKB signaling pathway. In some embodiments, TDs in a PTEN gene decrease PTEN protein activity. In some embodiments, TDs in a PTEN gene increase PTEN protein activity.

In some embodiments, a Group 1 TDP subtype, a Group 1/2mix TDP subtype, or a Group 1/3mix TDP subtype tumor sample has TDs in a RB1 gene (Gene ID: 5925). RB transcriptional corepressor 1 (RB1) negatively regulates the cell cycle and decreases gene expression by promoting heterochromatin stabilization. In some embodiments, TDs in a RB1 gene decrease RB1 protein activity. In some embodiments, TDs in a RB1 gene increase RB1 protein activity.

In some embodiments, a Group 1 TDP subtype, a Group 1/2mix TDP subtype, or a Group 1/3mix TDP subtype tumor has TDs in a NF1 gene (Gene ID: 4763). NF1 negatively regulates cell proliferation, division, and survival by decreasing the activity of the Ras signaling pathway. In some embodiments, TDs in a NF1 gene decrease NF1 protein activity. In some embodiments, TDs in a NF1 gene increase NF1 protein activity.

In some embodiments, the present disclosure provides a method for administering therapy to a subject having a Group 1 TDP subtype, a Group 1/2mix TDP subtype, or a Group 1/3mix TDP subtype tumor sample. In some embodiments, the therapy targets tumors comprising tandem duplications in PTEN, RB1, and/or NF1. In some embodiments, the therapy modulates the proliferation or survival of tumors comprising TDs in PTEN, RB1, and/or NF1. In some embodiments, the therapy decreases the proliferation or survival of tumors comprising TDs in PTEN, RB1, and/or NF1.

Group 1 TDP subtypes, Group 1/2mix TDP subtypes, and Group 1/3mix TDP subtype tumor samples have altered BRCA1 and/or p53 activity. In some embodiments, Group 1 TDP subtype, Group 1/2mix TDP subtype, and Group 1/3mix TDP subtype tumor samples have decreased BRCA1 and/or p53 activity. In some embodiments, Group 1 TDP subtype, Group 1/2mix TDP subtype, and Group 1/3mix TDP subtype tumor samples have increased BRCA1 and/or p53 activity.

The Breast cancer associated protein 1 (BRCA1) gene (Gene ID: 672) encodes the BRCA1 protein. The BRCA1 protein is a tumor suppressor that regulates transcription, DNA double-strand breaks, and recombination. Mutations in BRCA1 are responsible for about 40% of inherited breast cancers and more than 80% of inherited breast and ovarian cancers. In some embodiments, Group 1 TDP subtype, Group 1/2mix TDP subtype, and/or Group 1/3mix TDP subtype tumor samples have increased BRCA1 activity. In some embodiments, Group 1 TDP subtype, Group 1/2mix TDP subtype and/or Group 1/3mix TDP subtype tumor samples have decreased BRCA1 activity.

The tumor protein p53 (TP53) gene (Gene ID: 7157) encodes the TP53 protein. The TP53 protein regulates gene expression in response to cellular stresses. TP53 induces cell cycle arrest, apoptosis, senescence, DNA repair, and changes in metabolism. In some embodiments, Group 1 TDP subtype, Group 1/2mix TDP subtype, and/or Group 1/3mix TDP subtype tumor samples have increased TP53 activity. In some embodiments, Group 1 TDP subtype, Group 1/2mix TDP subtype, and/or Group 1/3mix TDP subtypes have decreased TP53 activity.

In some embodiments, therapy for a Group 1 TDP subtype, Group 1/2mix TDP subtype, and/or Group 1/3mix TDP subtype cancers include platinum-based agents. Platinum-based agents contain a platinum molecule conjugated to organic molecules including amines ($NH_2$), amides ($NH_3$), and chlorides (Cl). Platinum-based agents are effective at killing tumor cells because they are conjugated to DNA and inhibit DNA transcription, replication and repair. Non-limiting examples of platinum-based agents are cisplatin, carboplatin, oxaliplatin, nedaplatin, triplatin tetranitrate, phenanthriplatin, picoplatin, and satraplatin.

In some embodiments, therapy for a Group 1 TDP subtype, Group 1/2mix TDP subtype, and/or Group 1/3mix TDP subtype cancers include alkylating agents (e.g., cyclophosphamide, mechlorethamine, chlorambucil, melphalan, dacarbazine, nitroureas, temozolomide), anthracyclines (e.g., daunorubicin, doxorubicin, epirubucin, idarubicin, mitoxantrone, valrubicin), taxanes (e.g., paclitaxel, docetaxel, abraxane, taxotere), histone deacetylase inhibitors (e.g., vorinostat and romidepsin), topoisomerase inhibitors (e.g., irinotecan, topotecan, etoposide, teniposide, tafluposide), kinase inhibitors (e.g., bortezomib, erlotinib, gefitinib, imatinib, vemurafenib, vismodegib), nucleotide analogs (e.g., azacitidine, azathioprine, capecitabine, cytarabine, doxifluridine, fluorouracil, gemcitabine, hydroxyurea, mercaptopurine, methotrexate, tioguanine), retinoids (e.g., tretinoin, alitretinoin, bexarotene), and vinca alkaloids and derivatives (e.g., vinblastine, vincristine, vindesine, vinorelbine).

In some embodiments, administration of a therapy to a subject having a Group 1 TDP subtype, a Group 1/2mix TDP subtype, or a Group 1/3mix TDP subtype tumor modulates BRCA1 and/or p53 activity. Modulating can be increasing or decreasing BRCA1 and/or p53 activity. In some embodiments, therapy increases BRCA1 and/or p53 activity. In some embodiments, therapy decreases BRCA1 and/or p53 activity.

In some embodiments, therapy increases BRCA1 and/or p53 activity by 10%-500%. In some embodiments, therapy increases BRCA1 and/or p53 activity by 100%-1,000%. In some embodiments, therapy increases BRCA1 and/or p53 activity by 200%-500%. In some embodiments, therapy increases BRCA1 activity and/or p53 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

In some embodiments, therapy decreases BRCA1 and/or p53 activity by 10%-500%. In some embodiments, therapy decreases BRCA1 and/or p53 activity by 100%-1,000%. In some embodiments, therapy decreases BRCA1 and/or p53 activity by 200%-500%. In some embodiments, therapy decreases BRCA1 activity and/or p53 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

Group 2 TDP, Group 3 TDP, and Group 2/3mix TDP Subtypes

In some embodiments, when the tumor sample is assigned a Group 2 TDP subtype, a Group 2/3mix TDP subtype, or a Group 2/3mix TDP subtype, the method further comprises identifying a subject as a candidate for a therapy that targets tumors comprising TDs in ERBB2, MYC1, ESR1, MDM2, and/or lncRNA MALAT1.

In some embodiments, a Group 2 TDP subtype, a Group 3 TDP subtype, or a Group 2/3mix TDP subtype tumor sample has TDs in a ERBB2 gene (Gene ID: 2064). The erb-b2 receptor tyrosine kinase 2 (ERBB2) is an epidermal growth factor receptor that promotes cell division and cell proliferation. In some embodiments, TDs in a ERBB2 gene decreases ERBB2 protein activity. In some embodiments, TDs in a ERBB2 gene increases ERBB2 protein activity.

In some embodiments, a Group 2 TDP subtype, a Group 3 TDP subtype, or a Group 2/3mix TDP subtype tumor sample has TDs in a MYC1 gene (Gene ID: 4609). The MYC proto-oncogene, bHLH transcription factor 1 (MYC1) is a transcription factor that promotes cell cycle progression, apoptosis, and cellular transformation. In some embodiments, TDs in a MYC1 gene decreases MYC1 protein activity. In some embodiments, TDs in a MYC1 gene increases MYC1 protein activity.

In some embodiments, a Group 2 TDP subtype, a Group 3 TDP subtype, or a Group 2/3mix TDP subtype tumor sample has TDs in a MDM2 gene (Gene ID: 4193). The MDM2 proto-oncogene (MDM2) protein is a ubiquitin ligase that promotes tumor formation by stimulating the degradation of tumor suppressor proteins such as p53. In some embodiments, TDs in a MDM2 gene decreases MDM2 protein activity. In some embodiments, TDs in a MDM2 gene increases MDM2 protein activity.

In some embodiments, a Group 2 TDP subtype, a Group 3 TDP subtype, or a Group 2/3mix TDP subtype tumor sample has TDs in a long non-coding RNA (lncRNA) MALAT1 (Gene ID: 378938). The metastasis associated lung adenocarcinoma transcript 1 (MALAT1) lncRNA may act as a transcription regulator for genes involved in cell cycle regulation, cancer metastasis, and cell migration. In some embodiments, TDs in a MALAT1 lncRNA decreases MALAT1 activity. In some embodiments, TDs in a MALAT1 lncRNA increases MALAT1 activity.

In some embodiments, the present disclosure provides a method for administering therapy to a subject having a Group 2 TDP subtype, a Group 3 TDP subtype, or a Group 2/3mix TDP subtype tumor sample. In some embodiments, the therapy targets tumors comprising tandem duplications (TDs) in ERRB2, MYC1, ESR1, MDM2, and/or lncRNA MALAT1. In some embodiments, the therapy modulates the proliferation or survival of tumors comprising TDs in ERBB2, MYC1, ESR1, MDM2, and/or lncRNA MALAT1. In some embodiments, the therapy decreases the proliferation or survival of tumors comprising TDs in ERBB2, MYC1, ESR1, MDM2 and/or MALAT1.

Group 2 TDP subtypes, Group 3 TDP subtypes, and Group 2/3mix TDP subtype tumor samples have altered CCNE1, FBXW7, CDK12, and/or p53 activity. In some embodiments, Group 2 TDP subtype, Group 3 TDP subtype, and Group 2/3mix TDP subtype tumor samples have decreased CCNE1, FBXW7, CDK12, and/or p53 activity. In some embodiments, Group 2 TDP subtype, Group 3 TDP subtype, and Group 2/3mix TDP subtype tumor samples have increased CCNE1, FBXW7, CDK12, and/or p53 activity.

The cyclin E1 (CCNE1) gene (Gene ID: 898) encodes the CCNE1 protein. The CCNE1 protein regulates the cell cycle. Overexpression of CCNE1 occurs in numerous types of cancers. In some embodiments, Group 2 TDP subtype, Group 3 TDP subtype, and/or Group 2/3mix TDP subtype tumor samples have increased CCNE1 activity. In some embodiments, Group 2 TDP subtype, Group 3 TDP subtype and/or Group 2/3mix TDP subtype tumor samples have decreased CCNE1 activity.

The F-box and WD repeat domain containing 7 (FBXW7) gene (Gene ID: 55294) encodes the FBXW7 protein. The FBXW7 protein is a ubiquitin ligase which negatively regulates the cell cycle through degradation of cyclin E. Mutations in FBXW7 occur in some ovarian and breast cancers. In some embodiments, Group 2 TDP subtype, Group 3 TDP subtype, and/or Group 2/3mix TDP subtype tumor samples have increased FBXW7 activity. In some embodiments, Group 2 TDP subtype, Group 3 TDP subtype, and/or Group 2/3mix TDP subtype tumor samples have decreased FBXW7 activity.

The cyclin dependent kinase 12 (CDK12) gene (Gene ID: 51755) encodes the CDK12 protein. The CDK12 protein regulates the transcription of genes involved in DNA repair, cell proliferation, and cell division. In some embodiments, Group 2 TDP subtype, Group 3 TDP subtype, and/or Group 2/3mix TDP subtype tumor samples have increased CDK12 activity. In some embodiments, Group 2 TDP subtype, Group 3 TDP subtype, and/or Group 2/3mix TDP subtype tumor samples have decreased CDK12 activity.

The tumor protein p53 (TP53) gene (Gene ID: 7157) encodes the TP53 protein. The TP53 protein regulates gene expression in response to cellular stresses. TP53 induces cell cycle arrest, apoptosis, senescence, DNA repair, and changes in metabolism. In some embodiments, Group 2 TDP subtype, Group 3 TDP subtype, and/or Group 2/3mix TDP subtype tumor samples have increased TP53 activity. In some embodiments, Group 2 TDP subtype, Group 3 TDP subtype, and/or Group 2/3mix TDP subtypes have decreased TP53 activity.

In some embodiments, therapy for a Group 2 TDP subtype, Group 3 TDP subtype, and/or Group 2/3mix TDP subtype cancers include platinum-based agents. Non-limiting examples of platinum-based agents are cisplatin, carboplatin, oxaliplatin, nedaplatin, triplatin tetranitrate, phenanthriplatin, picoplatin, and satraplatin.

In some embodiments, therapy for a Group 2 TDP subtype, Group 3 TDP subtype, and/or Group 2/3mix TDP subtype cancers include alkylating agents (e.g., cyclophosphamide, mechlorethamine, chlorambucil, melphalan, dacarbazine, nitroureas, temozolomide), anthracyclines (e.g., daunorubicin, doxorubicin, epirubicin, idarubicin, mitoxantrone, valrubicin), taxanes (e.g., paclitaxel, docetaxel, abraxane, taxotere), histone deacetylase inhibitors (e.g., vorinostat and romidepsin), topoisomerase inhibitors (e.g., irinotecan, topotecan, etoposide, teniposide, tafluposide), kinase inhibitors (e.g., bortezomib, erlotinib, gefitinib, imatinib, vemurafenib, vismodegib), nucleotide analogs (e.g., azacitidine, azathioprine, capecitabine, cytarabine, doxifluridine, fluorouracil, gemcitabine, hydroxyurea, mercaptopurine, methotrexate, tioguanine), retinoids (e.g., tretinoin, alitretinoin, bexarotene), and vinca alkaloids and derivatives (e.g., vinblastine, vincristine, vindesine, vinorelbine).

In some embodiments, administration of a therapy to a subject having a Group 2 TDP subtype, a Group 3 TDP subtype, or a Group 2/3mix TDP subtype tumor modulates CCNE1, FBXW7, CDK12 and/or p53 activity. Modulating can be increasing or decreasing CCNE1, FBXW7, CDK12 and/or p53 activity. In some embodiments, therapy increases CCNE1, FBXW7, CDK12 and/or p53 activity. In some embodiments, therapy decreases CCNE1, FBXW7, CDK12 and/or p53 activity.

In some embodiments, therapy decreases CCNE1 activity. In some embodiments, therapy decreases CCNE1 activity by 10%-500%. In some embodiments, therapy decreases CCNE1 activity by 100%-1,000%. In some embodiments, therapy decreases CCNE1 activity by 200%-500%. In some embodiments, therapy decreases CCNE1 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

In some embodiments, therapy increases FBXW7 activity. In some embodiments, therapy increases FBXW7 activity by 10%-500%. In some embodiments, therapy increases FBXW7 activity by 100%-1,000%. In some embodiments, therapy increases FBXW7 activity by 200%-500%. In some embodiments, therapy increases FBXW7 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

In some embodiments, therapy decreases CDK12 activity. In some embodiments, therapy decreases CDK12 activity by 10%-500%. In some embodiments, therapy decreases CDK12 activity by 100%-1,000%. In some embodiments, therapy decreases CDK12 activity by 200%-500%. In some embodiments, therapy decreases CDK12 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

In some embodiments, therapy increases p53 activity. In some embodiments, therapy increases p53 activity by 10%-500%. In some embodiments, therapy increases p53 activity by 100%-1,000%. In some embodiments, therapy increases p53 activity by 200%-500%. In some embodiments, therapy increases p53 activity by 10%, 20%, 30%, 40%, 50%, 60%, 70%, 80%, 90%, 100%, 120%, 140%, 160%, 180%, 200%, 220%, 240%, 260%, 280%, 300%, 320%, 340%, 360%, 380%, 400%, 420%, 440%, 460%, 480%, or 500%.

EXAMPLES

Example 1. TD Span Distribution Profiles Classify TDP Tumors into Six Distinct Subgroups To explore the different configurations of the TDP in detail, we first analyzed TD number and genomic distribution (i.e., TDP score [Menghi et al., 2016]) across the entire Cancer Genome Atlas (TCGA) WGS dataset, comprising 25 distinct tumor types. Of the 992 TCGA cancer genomes analyzed, 118 (11.9%) were classified as TDP (data not shown). We examined the TD span size distribution of each individual TDP tumor and observed only a few recurrent patterns, each one characterized by either a modal or a bimodal profile (FIG. 1A). We systematically classified these recurrent profiles by binning all of the modal peaks relative to the TD span size distributions observed across 118 identified TDP tumors in this dataset into five non-overlapping intervals, based on the best fit of a Gaussian finite mixture model (see the STAR Methods). We then labeled the TDs corresponding to the five span size intervals as class 0: <1.6 kb in span size; class 1: between 1.64 and 51 kb (median value of 11 kb); class 2: between 51 and 622 kb (median value of 231 kb); class 3: between 622 kb and 6.2 Mb (median value of 1.7 Mb); and class 4: >6.2 Mb (data not shown). Noticeably, classes 1-3 made up almost 95% (146/154) of all the identified modal peaks (data not shown).

Figure 1B:
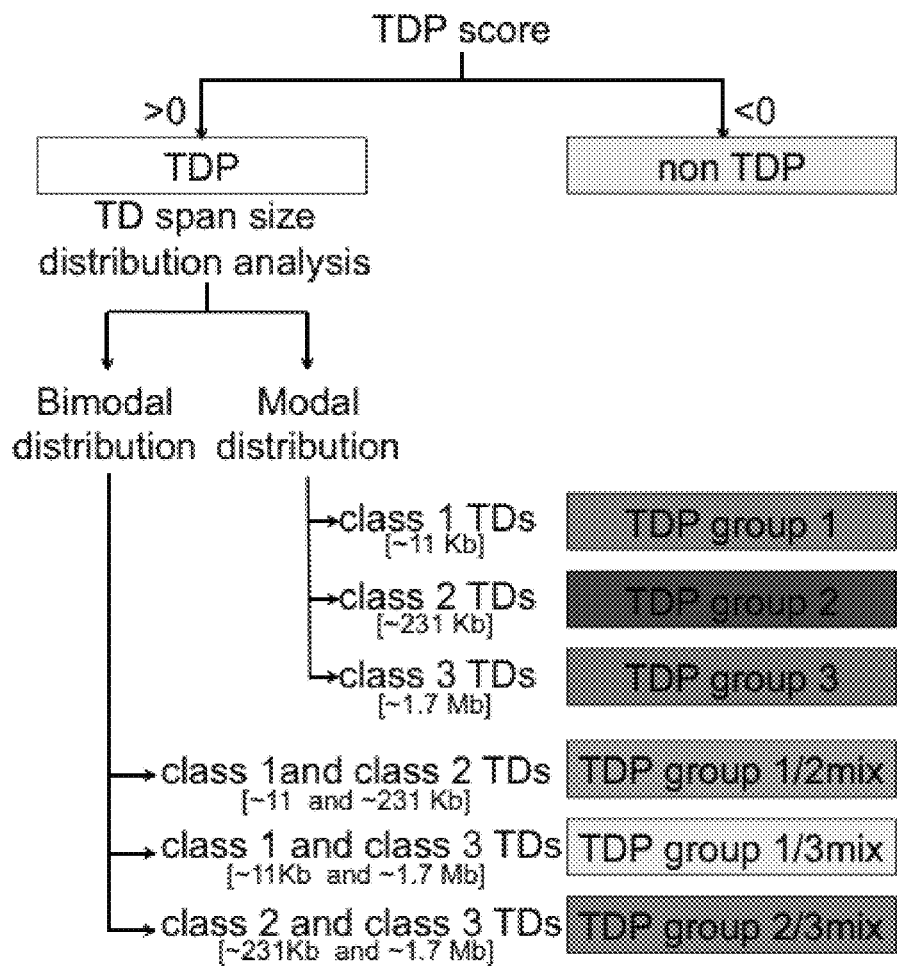

Using this classification, we were able to stratify TDP tumors into six distinct subgroups. Tumors with a modal TD span size distribution were designated as TDP group 1, group 2, or group 3, based on the presence of a single class 1 (11 kb), class 2 (231 kb), or class 3 (1.7 Mb) TD span size distribution peak, respectively. Tumors that showed a bimodal TD span size profile were designated as TDP group 1/2mix (featuring both a class 1 and a class 2 TD span size distribution peaks), group 1/3mix (class 1 and class 3 peaks), or group 2/3mix (class 2 and class 3 peaks; FIGS. 1A and 1B). Only 1/118 tumors (0.8%) could not be classified into any of the six identified TDP subgroups, since it featured only very small or very large TDs (<1.6 kb, i.e., class 0; and >6.2 Mb, i.e., class 4), and was excluded from further analysis. Thus, virtually all of the TDP tumors analyzed exhibited clearly distinct TD span size distributions converging on one of only three highly recurrent and narrowly ranged span size intervals. These data strongly suggest that specific, distinct mechanisms of DNA instability are at play in the identified TDP subgroups.

Figure 1C:
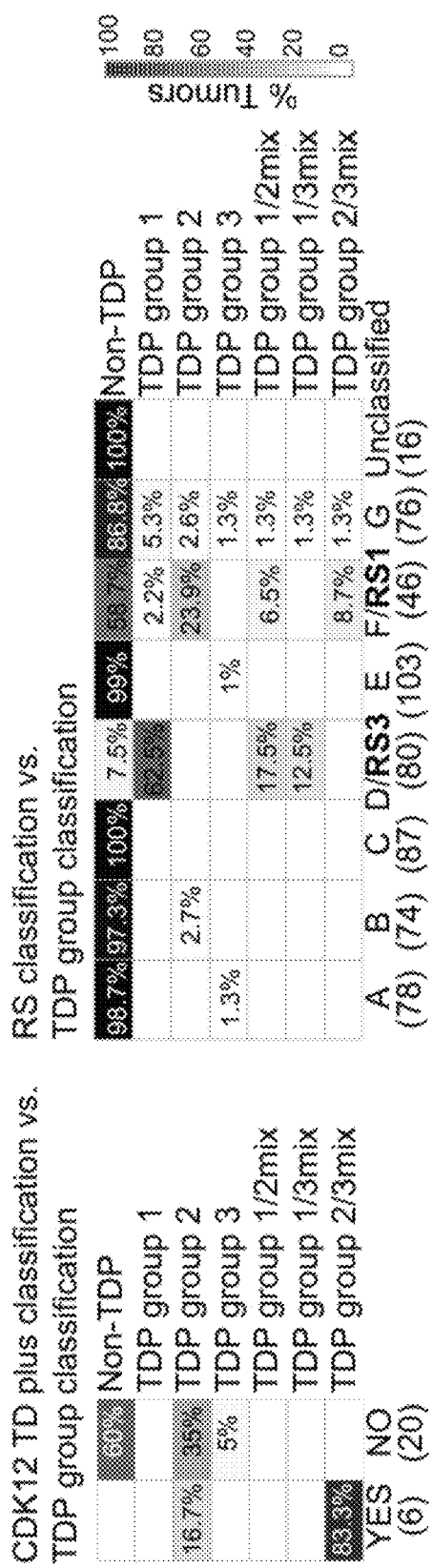

When compared with the recently described TD-based genomic signatures (Nik-Zainal et al., 2016; Popova et al., 2016), our TDP classification algorithm classified 83% (5/6) of the reported CDK12 TD plus phenotype-positive tumors as TDP group 2/3mix (FIG. 1C). It also classified 93% (74/80) of RS3-positive tumors as TDP groups 1, 1/2mix, or 1/3mix; but only 39% (18/46) of RS1-positive tumors as TDP group 2, 1/2mix, or 2/3mix, with most of the remaining 61% (27/46) classifying as non-TDP (FIG. 1C). On closer inspection, most of the tumors classified as RS1 that were not designated as TDP featured only a small number of TDs (<15), and did not pass the TDP score threshold. Since our threshold was defined by a statistical segregation of a distinctive cancer genomic configuration, these subthreshold RS1-positive tumors are likely not to represent a specific mechanistic origin but a general characteristic of cancer. Thus, collectively, there is a consensus that a specific form of genomic instability characterized by accumulation of TDs, which we call the TDP, exists in cancer. Our classification approach, however, simplifies and unifies the identification of the TDP by generating a single score and provides refined sub-classifications based on TD span size.

Example 2. TDP Subgroups Occur at Different Frequencies Across Different Tumor Types We validated our classification scheme on a separate pan-cancer dataset of whole-genome sequences relative to 1,725 tumor samples from individual patient donors, assembled from 30 independent studies (see the Method). A total of 258/1725 (15%) tumors were classified as TDP, and over 99% of these (257/258) matched one of the six identified TDP subgroup profiles (data not shown), indicating that our classification scheme performs consistently and robustly across different tumor types and datasets.

Figure 1D:
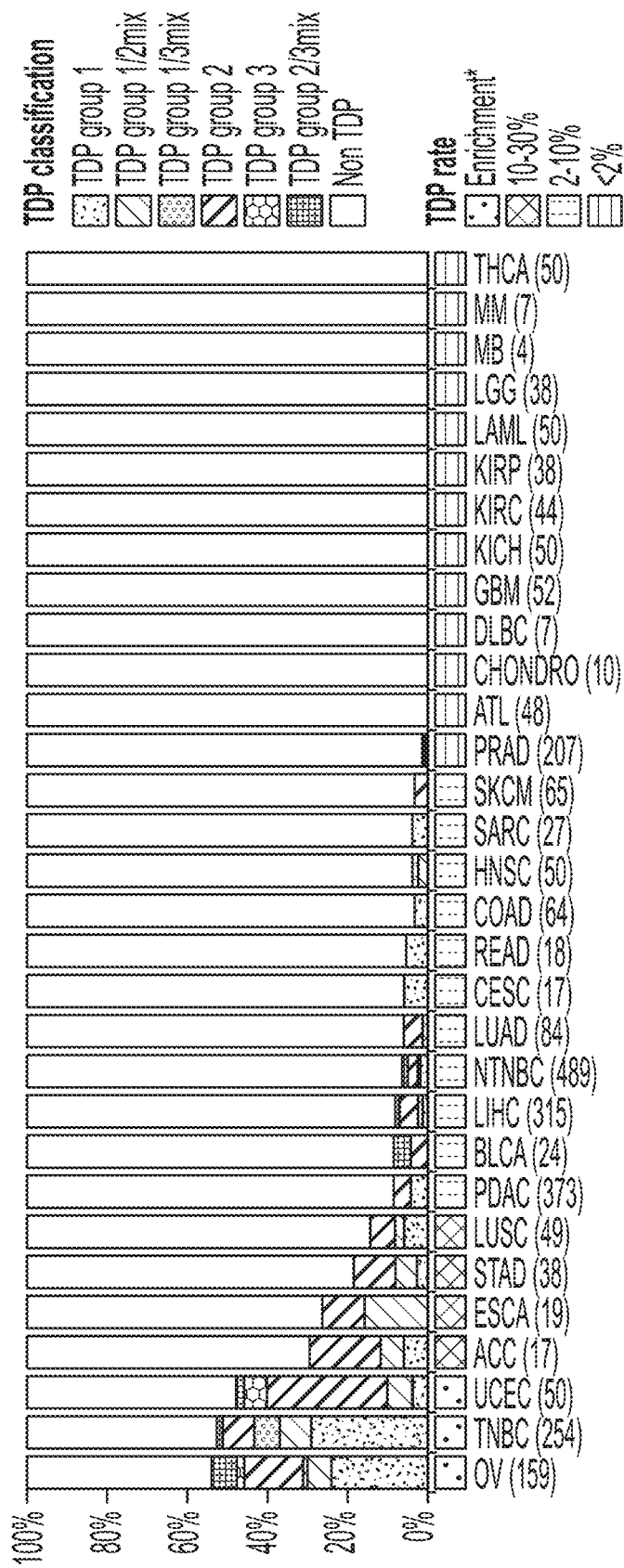

When combined with the TCGA training set, we analyzed a total of 2,717 independent tumor genomes, of which 375 (13.8%) classified as TDP (data not shown). Using this large dataset, we confirmed that the TDP is not a ubiquitous characteristic of cancer. In fact, whereas the TDP occurred in _50% of triple negative breast cancer (TNBC), ovarian carcinoma (OV), and endometrial carcinoma (UCEC), it was found in 10%-30% of adrenocortical, esophageal, stomach, and lung squamous carcinomas, and in only 2%-10% of a variety of other cancer types including pancreatic, liver, non-triple-negative breast, and colorectal carcinomas. Finally, the TDP was absent in leukemia, lymphoma, glioblastoma, prostate, and thyroid carcinomas, and all forms of kidney cancer (FIG. 1D; data not shown). Of note, the six TDP subgroups recurred among the few highly TDP-enriched tumor types, but at significantly different relative frequencies (FIG. 1D). Whereas the TDP was found in almost half of all TNBC, OV, and UCEC tumors (52.8%, 54.1%, and 48%, respectively), TDP group 1 accounted for 29% (74/254) of all TNBCs and 24% (38/159) of OV cancers, but only for 4% (2/50) of UCEC tumors. Conversely, 30% of UCEC but only 7% of TNBCs and 15% of OV cancers classified as TDP group 2 (FIG. 1D; data not shown). Intriguingly, the vast majority of TDP UCEC tumors were of serous histology (66.7% versus 11.5% of non-TDP tumors, $p=9.6 \times 10\_5$; Fisher's test) and were highly enriched for the copy-number high-molecular subtype (91.6% versus 19.2% of non-TDP tumors, $p=1.8 \times 10\_7$), while being depleted for the microsatellite instability (MSI) profile (4.2% versus 34.6% of non-TDP tumors, $p=0.01$) (Cancer Genome Atlas Research Network et al., 2013). Taken together, these observations suggest that certain defined molecular differences must exist that guide the formation of the distinct TDP subtypes, which are distinct from those associated with the MSI form of genomic instability.

Figure 2A:
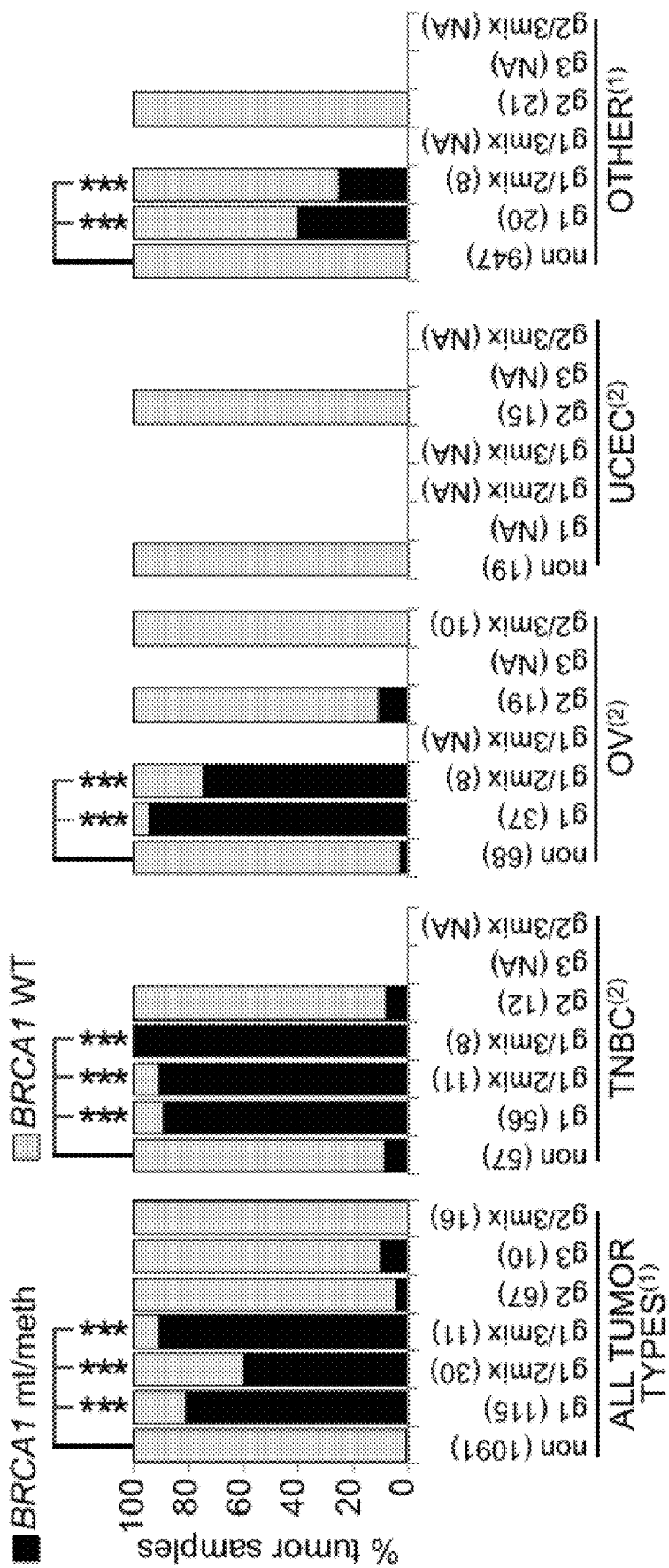

Example 3. Joint Abrogation of Both BRCA1 and p53 Specifically Drives the Emergence of the TDP Group 1 Configuration When we looked for specific mutations that may distinguish the different TDP profiles, the most prominent observation was that TDP subgroups characterized by a prevalence of short-span TDs (class 1, _11 kb), either alone (i.e., TDP group 1) or in combination with larger TDs (i.e., TDP groups 1/2mix and 1/3mix), were tightly associated with BRCA1 deficiencies, including somatic (8.4%) or germline gene mutation (48.7%), promoter hyper-methylation (42%), or structural rearrangement (0.9%) (FIG. 2A). Indeed, in the pan-cancer dataset, <2% of non-TDP tumors showed BRCA1 deficiencies, compared with 80.9% of TDP group 1, 60% of TDP group 1/2mix, and 90.9% of TDP group 1/3mix tumors. Importantly, this association was even stronger when analyzing the TNBC and OV datasets individually, where BRCA1 abrogation was present in at least 75% and up to 100% of tumors in TDP groups 1, 1/2mix, and 1/3mix (FIG. 2A; data not shown). By contrast, less than 10% of non-TDP and TDP groups 2 or 3 tumors across the TNBC and OV datasets showed BRCA1 deficiencies.

Whereas BRCA1 deficiency highly enriched for TDP profiles comprising predominantly short-span TDs, either alone or in combination with larger TDs, BRCA2 disruptions were not statistically linked to any TDP configurations (data not shown). In fact, we found BRCA2 mutations to be significantly depleted from TDP group 1 in the pan-cancer dataset and from TDP groups 1 and 2 in the OV dataset (data not shown), corroborating our previous finding of decreased BRCA1, but not BRCA2, expression levels in TDP tumors (Menghi et al., 2016).

Figure 2B:
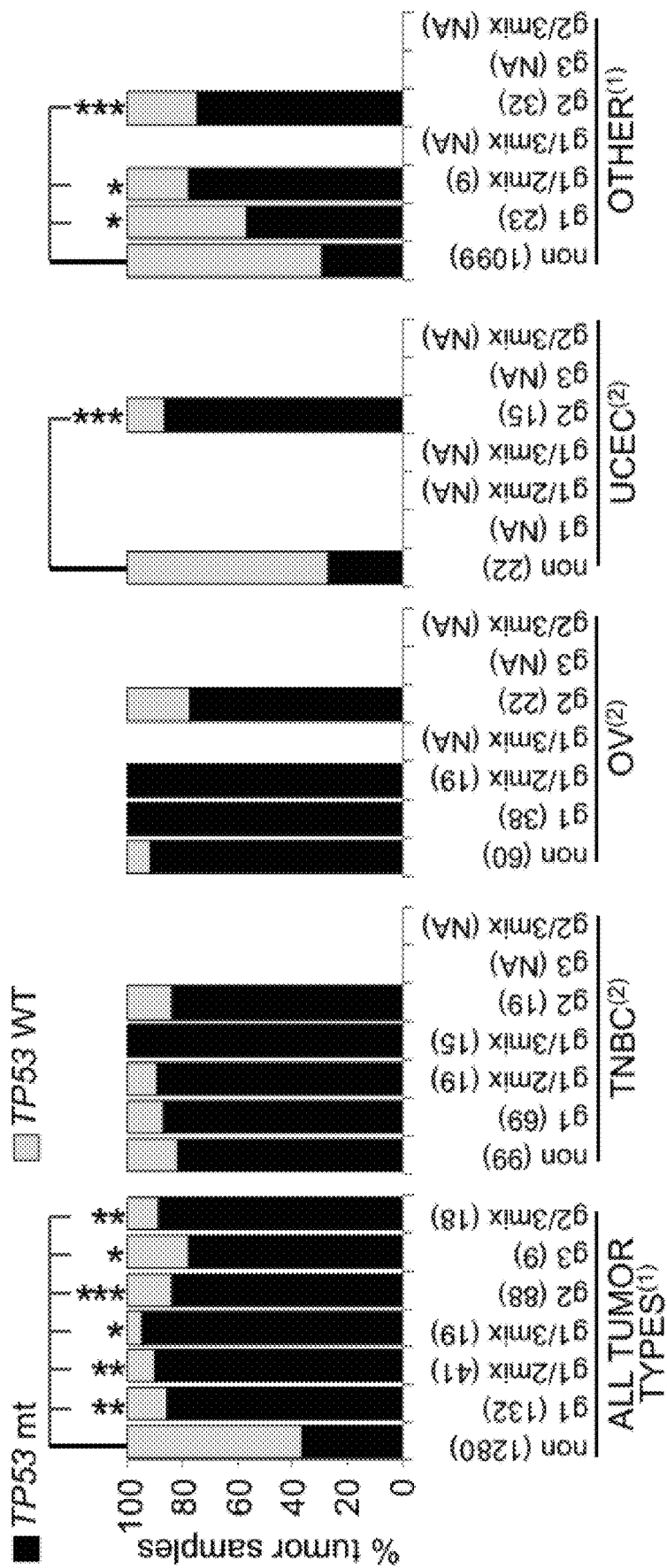

When considering the entire pan-cancer dataset, we observed a second highly prevalent mutation associated with TDP: TP53 featured significantly higher rates of somatic mutations in all TDP groups versus non-TDP tumors (86.3% mutation rate in TDP versus 36.7% in non-TDP; data not shown) and across each distinct TDP subgroup when compared with non-TDP tumors (36.7% mutation rate in non-TDP versus 85.6% in TDP group 1, 84.1% in TDP group 2, 77.8% in TDP group 3, 90.2% in TDP group 1/2mix, 94.7% in TDP group 1/3mix, and 88.9% in TDP group 2/3mix; FIG. 2B and data not shown). Of note, these significant associations persisted after adjusting for BRCA1 status in a multivariate analysis (data not shown). Statistical association between TP53 mutational status and TDP could not be found when analyzing the TNBC and OV datasets separately only because TP53 is mutated in virtually 100% of TNBC (194/226; data not shown) and OV (138/140; data not shown). However, a strong association between functional loss of TP53 and TDP status was observed in the UCEC dataset, where >85% of TDP group 2 tumors have a somatic mutation of TP53 compared with <28% of non-TDP tumors (FIG. 2B; data not shown). Taken together, these data suggest that TP53 mutations are necessary but not sufficient for the development of all forms of TDP-related genomic instabilities. Importantly, the conjoint abrogation of both p53 and BRCA1 was found in >72% of all TNBC and OV TDP samples with class 1 TDs (i.e., TDP groups 1, 1/2mix, and 1/3mix), but only in <10.5% of all other TDP groups and <4.7% in non-TDP tumors (data not shown), suggesting that TDPs with class 1 TDs may require both proteins to be abrogated for TDP formation.

Figure 2D:
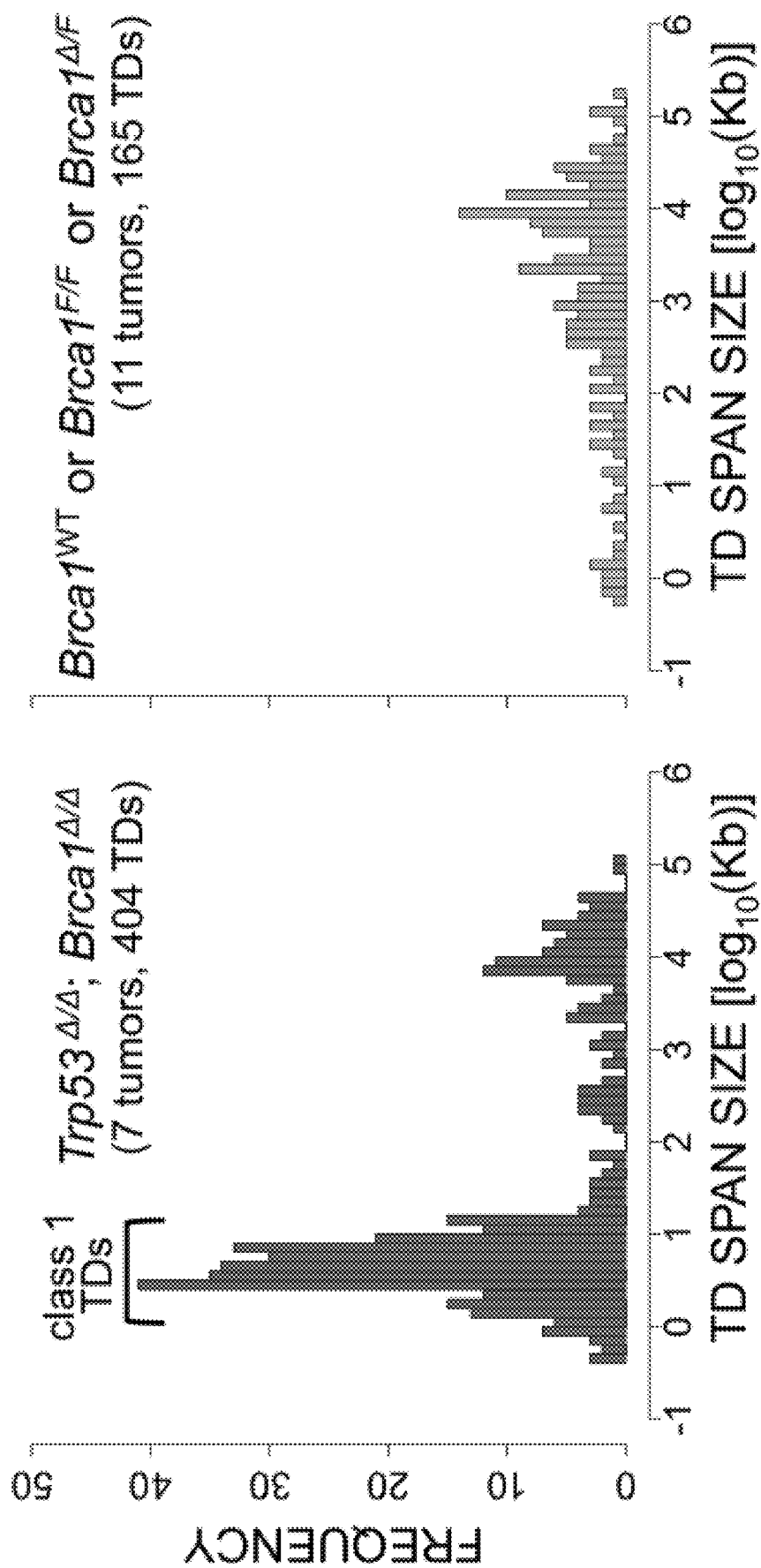

Using genetically modified mouse models of mammary cancer, we sought to definitely determine the roles of p53, BRCA1, and BRCA2 in generating the genomic pattern typical of TDP group 1. We analyzed the genomes of 18 mouse breast cancers caused by the targeted tissue-specific deletion of Trp53 alone (KP, n=3; WP, n=3) or in combination with Brca1 (KB1P, n=3; WB1P, n=3), Brca2 (KB2P, n=3) or both Brca1 and Brca2 (KB1B2P, n=3) (Jonkers et al., 2001; Liu et al., 2007). Using the identical scoring algorithm for TDP as used in human tumor samples, we found the precise configuration of TDP group 1 only in tumors with homozygous deletions of both Trp53 and Brca1 (FIG. 2C; data not shown). However, there was no evidence of combined modal peaks represented by the group 1/2mix and 1/3mix configurations. Of the six tumors specifically testing the combined homozygous deletion of Trp53 and Brca1 showing a Trp53 D/D; Brca1D/D genotype, five were classified as TDP group 1. Similar to the human TDP group 1 tumors, the murine mammary cancers exhibited short TD spans of 2.5-11 kb (median value=6.3 kb; FIG. 2D). The remaining Trp53 D/D; Brca1D/D tumor that was not scored as TDP had the appropriate TD class 1 modal peak but did not achieve the strict numerical threshold to be called a TDP tumor (TDP score=_0.23, with cut off being 0) (FIG. 2C). None of the tumors arising from sole disruption of Trp53, or of Trp53 and Brca2, showed any TDP characteristics (FIG. 2C; data not shown). In tumors arising from mice with the intention of knocking out Trp53, Brca1, and Brca2 simultaneously, we observed that whereas Trp53 and Brca2 were affected by homozygous deletions across all three tumors, Brca1 was found to exhibit homozygous deletion in only one tumor. Importantly, this was the only tumor among the three that classified as TDP group 1. The remaining two tumors were non-TDP and maintained either one or both functional copies of Brca1 (FIG. 2C; data not shown). These data provide the experimental proof that the TDP group 1 configuration is a universal and specific feature of BRCA1-linked breast tumorigenesis, emerging in the context of a TP53 null genotype. This also implies that BRCA1 haploinsufficiency is not sufficient to induce the TDP in the presence of TP53 loss, despite recent evidence that it may indeed contribute to the transformation of normal mammary epithelial cells (Pathania et al., 2011). Also, not only does BRCA2 deficiency not induce any form of TDP, our observations suggest that abrogation of BRCA2 does not suppress TD formation in the presence of BRCA1 deficiency. Finally, the absence of any bimodal peak configurations (i.e., TDP groups 1/2mix or 1/3mix) in the mouse tumors suggests that additional mutations may be necessary to drive the mixed forms of TDP.

Figure 3A:
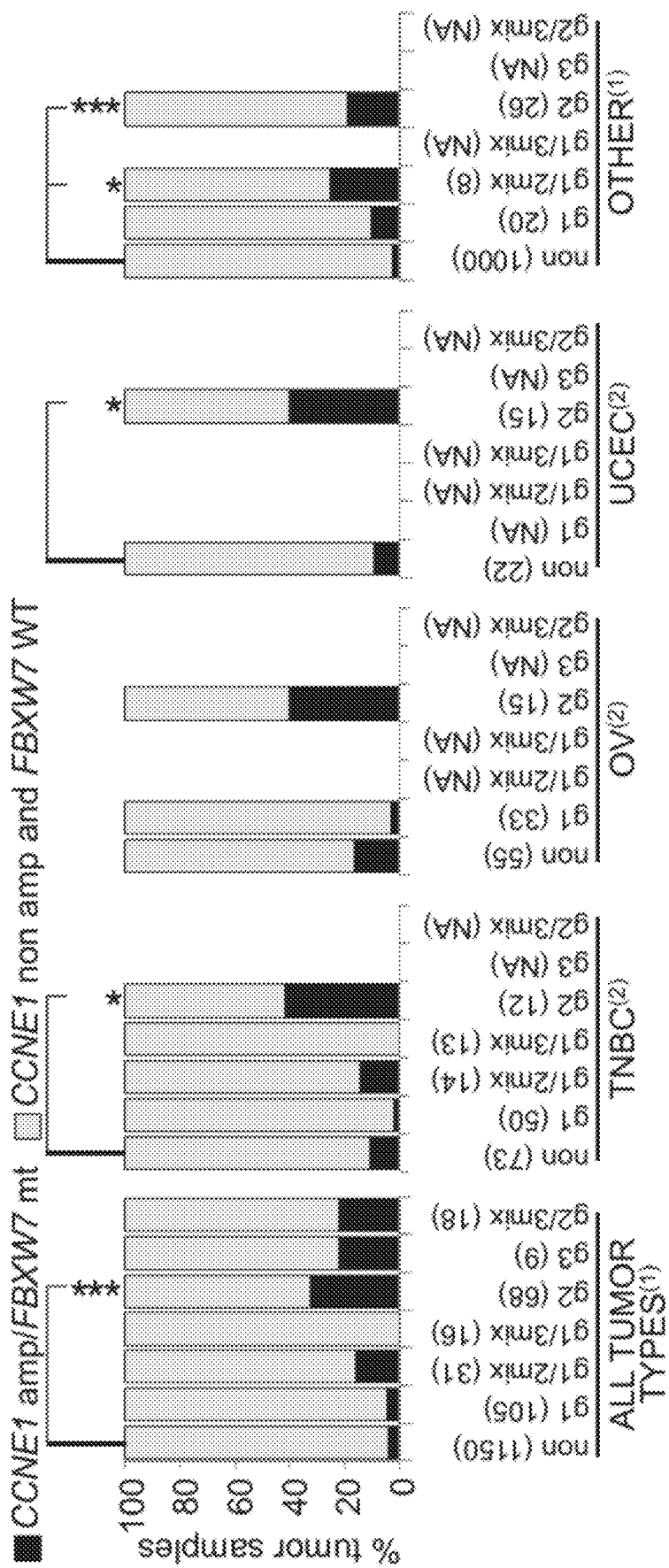
FIGS. 3A-3B. Genetic Perturbations Associated with BRCA1-Proficient TDP Groups.

Example 4. Identification of the Genetic Perturbations Driving Non-BRCA1-Linked TDP Groups to Identify Potential Genetic Drivers for the Non-BRCA1-Linked TDP Groups TDPs, we compared rates of gene perturbation by somatic single nucleotide variation across different TDP subgroups. In the initial discovery phase, we analyzed tumor samples in the breast, OV, and UCEC cancer datasets, which comprised the highest number of TDP tumors, and compared individual gene mutation rates across tumor subgroups, searching for genes whose mutation rate was significantly higher in non-BRCA1-linked TDP groups compared with TDP group 1 and with non-TDP tumors (see the STAR Methods). CDK12 emerged as the strongest candidate linked to the TDP group 2/3mix profile, showing disruptive mutations in 26.7% of TDP group 2/3mix tumors, compared with 0% of TDP group 1 (p=2.3 3 10_4, Fisher's test) and <1% of non-TDP tumors (p=4.0 3 10_5, Fisher's test; data not shown). Also, as reported previously (Popova et al., 2016), when looking at CDK12 mutation rates within individual tumor types, the highest frequency of mutation occurred in the OV subset, where disruption of CDK12 by somatic mutation explained 60% (6/10) of all TDP group 2/3mix tumors, but was absent in TDP group 1 (0/27) and in non-TDP (0/45) tumors (FIG. 3A; data not shown). Taken together, these results confirm the existence of a CDK12-linked genomic instability profile characterized by TDs of specifically large span size.

Figure 3B:
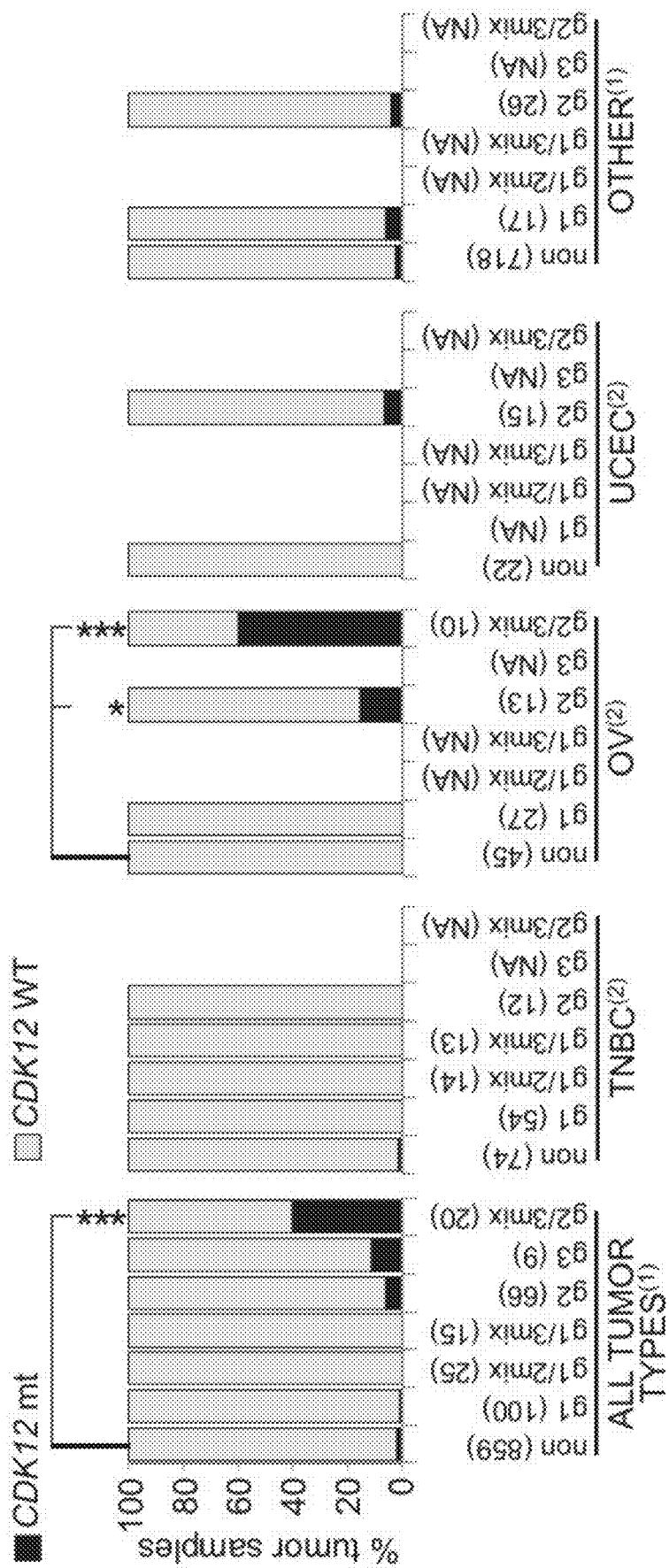

When focusing on TDP group 2 tumors, the strongest association involved FBXW7, which was mutated in 11.5% of TDP group 2 tumors, compared with 2.1% of TDP group 1 (p=2.3 3 10_2, Fisher's test) and 1.3% of non-TDP tumors (p=4.4310_4; data not shown). Although significant, the disruption of FBXW7 could only explain a modest fraction of all TDP group 2 tumors. We therefore hypothesized that other genes may contribute to this profile by virtue of copy-number variation (CNV). To explore this possibility, we focused on the TCGA dataset and examined CNV profiles that might be associated with TDP group 2 using a linear mixed model analysis (see the Methods). The top six genes ranked in this analysis were all part of the 19q12 amplicon that is frequently found in ovarian, breast, and endometrial carcinomas, and that comprises CCNE1 (Etemadmoghadam et al., 2013) (data not shown). The FBXW7 protein is known to act as a negative regulator of CCNE1 activity by binding directly to the CCNE1 protein and targeting it for ubiquitin-mediated degradation (Klotz et al., 2009). Thus, FBXW7 disruptive mutations might phenocopy CCNE1 amplification, therefore independently contributing to the same oncogenic pathway. When assessing the frequency of CCNE1 pathway activation defined by the presence of either FBXW7 somatic damaging mutations or CCNE1 amplification (R6 gene copies), 32.4% of TDP group 2 tumors scored positively, compared with <5% of non-TDP tumors and TDP group 1 tumors (FIG. 3B; data not shown). Specifically, in each one of the individual TNBC, OV, and UCEC datasets, CCNE1 pathway activation was found to explain at least 40% of TDP group 2 tumors (FIG. 3B). CCNE1 was neither a hotspot for TD formation in TDP tumors (see below) nor was it perturbed by the class 2 TDs characteristic of TDP group 2. In fact, only in 3% of CCNE1 amplifications featured a class 2 TD. Importantly the significant association between CCNE1 pathway activation and TDP status was maintained when those tumor samples where a class 2 TD duplicated the CCNE1 gene were removed from the analysis (data not shown), supporting the hypothesis that CCNE1 activation is a cause rather than a consequence of the TDP group 2 configuration.

Example 5. TD Breakpoint Hotspots

Figure 4A:
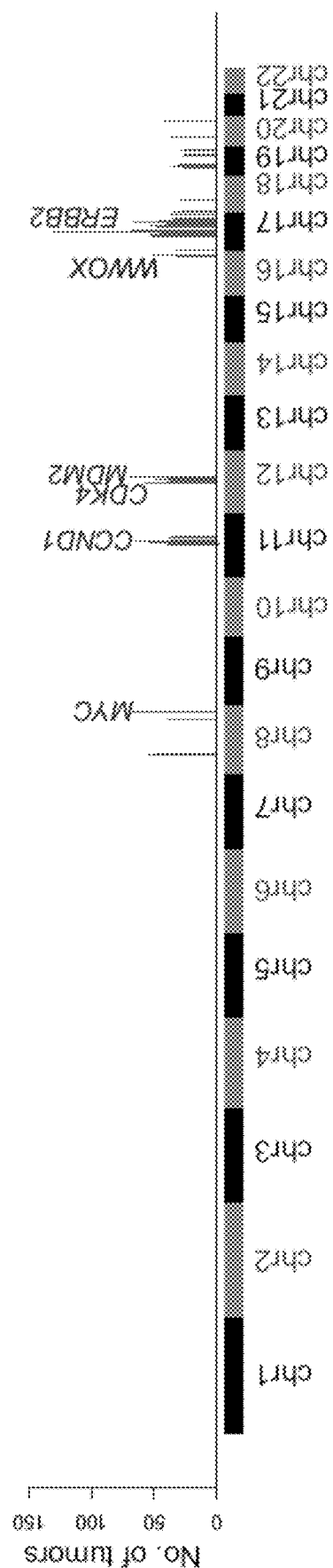
FIGS. 4A-4B. Genomic Hotspots of TD Breakpoints.
Figure 4B:
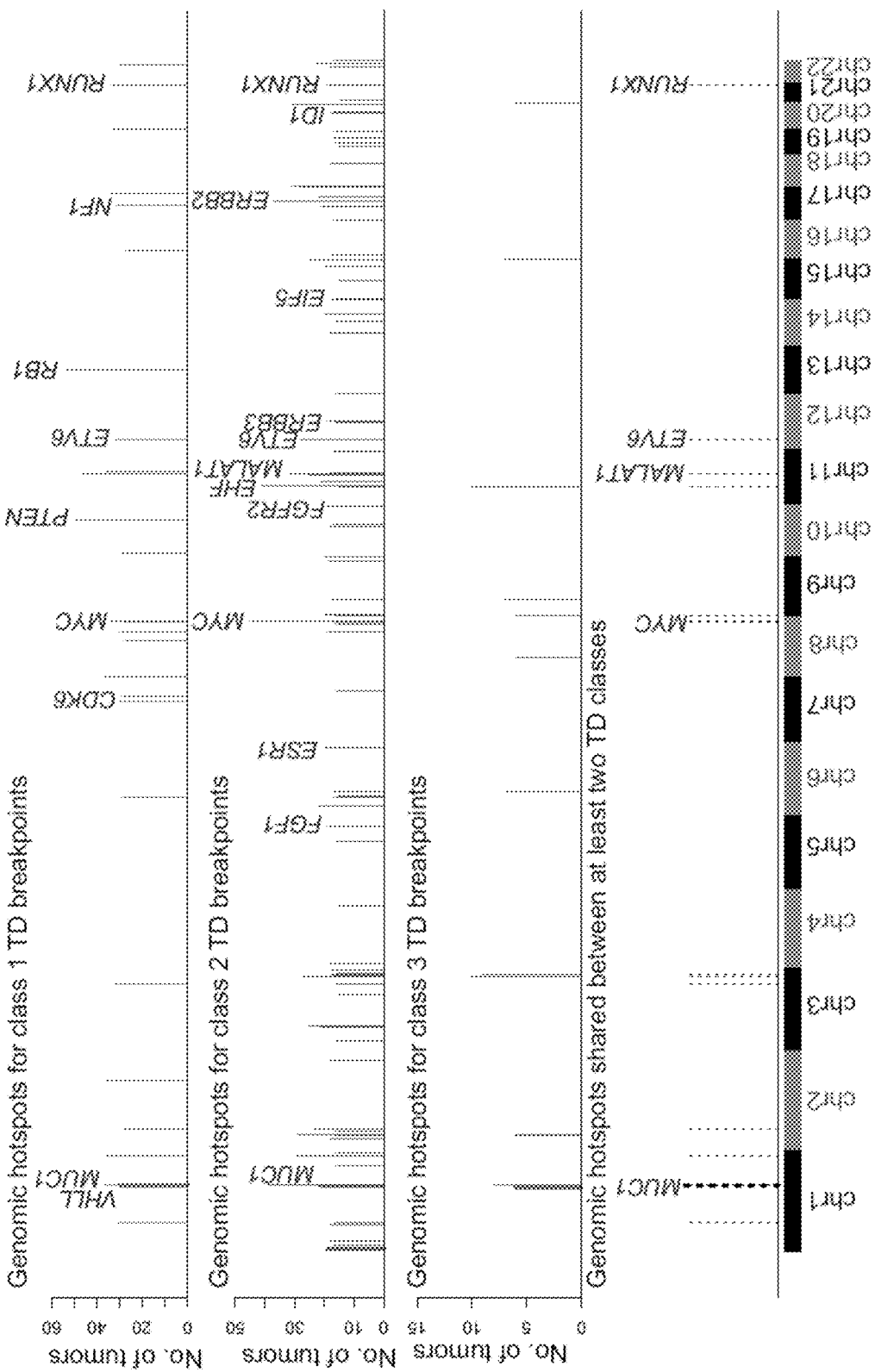

We hypothesized that certain genomic loci may be targeted for TD formation and that these loci would differ across different TDPs. To address this possibility, we counted the number of TD breakpoints falling into consecutive 500-kb genomic windows for each one of the four major sets of TDs observed across the pan-cancer dataset (i.e., class 1 TDs [_11 kb], class 2 TDs [_231 kb], class 3 TDs (_1.7 Mb), and non-TDP TDs; data not shown), We then identified genomic hotspots as 500-kb windows with an observed number of breakpoints significantly larger than expected (see the Methods). A total of 245 genomic windows were identified as genomic hotspots for TD breakpoints (data not shown). Importantly, the overall genomic distribution of the significant hotspots was very different when comparing the four TD classes. Most of the 101 genomic hotspots relative to the non-TDP TD breakpoints tightly clustered across a small number of distinct genomic regions that have been reported to be frequently involved in oncogene amplification (i.e., ERBB2, MYC, CCND1, CDK4, and MDM2; FIG. 4A). This confirms our previous report that TDs are commonly implicated in nucleating amplicon formation in regions of gene amplification in cancer (Inaki et al., 2014). By contrast, the TDP genomic hotspots were more uniformly scattered along the genome (FIG. 4B) and they appeared to engage different sets of oncogenic elements, with tumor suppressor genes (TSGs) and oncogenes being commonly found within the genomic hotspots identified for class 1 and class 2 TDs, respectively (FIG. 4B and see below).

Of note, despite the fact that the number of class 1 TDs was more than double that of class 2 TDs (22,447 class 1 TDs versus 9,794 class 2 TDs), there was a larger number of class 2 TD breakpoint hotspots compared with class 1 (102 versus 30), suggesting greater selectivity for the formation of the short-span class 1 TDs (data not shown).

Figure 5A:
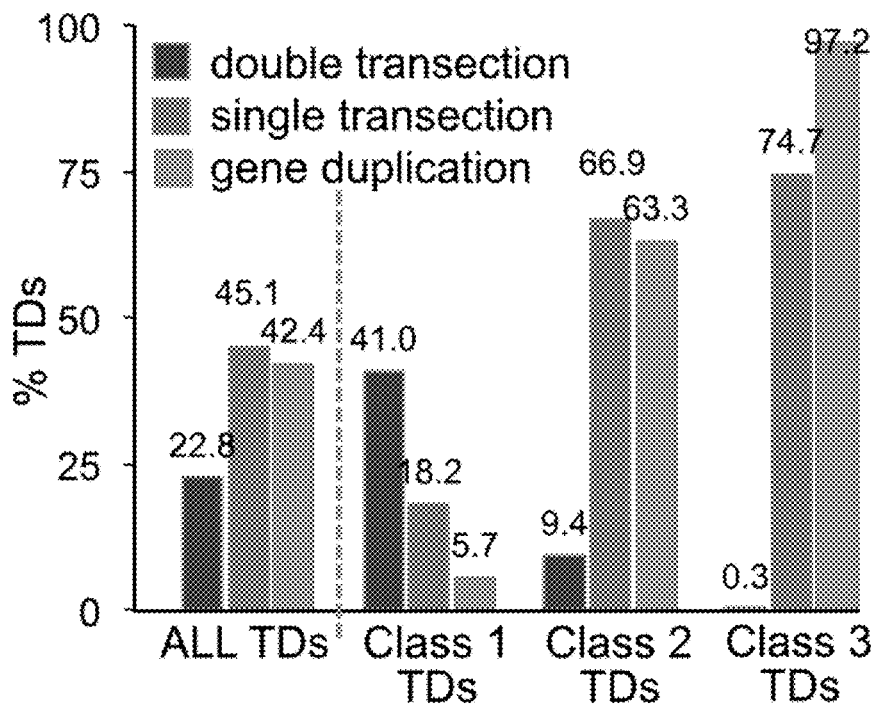
FIGS. 5A-5G. TD-Mediated Effects on Gene Bodies.
Figure 5B:
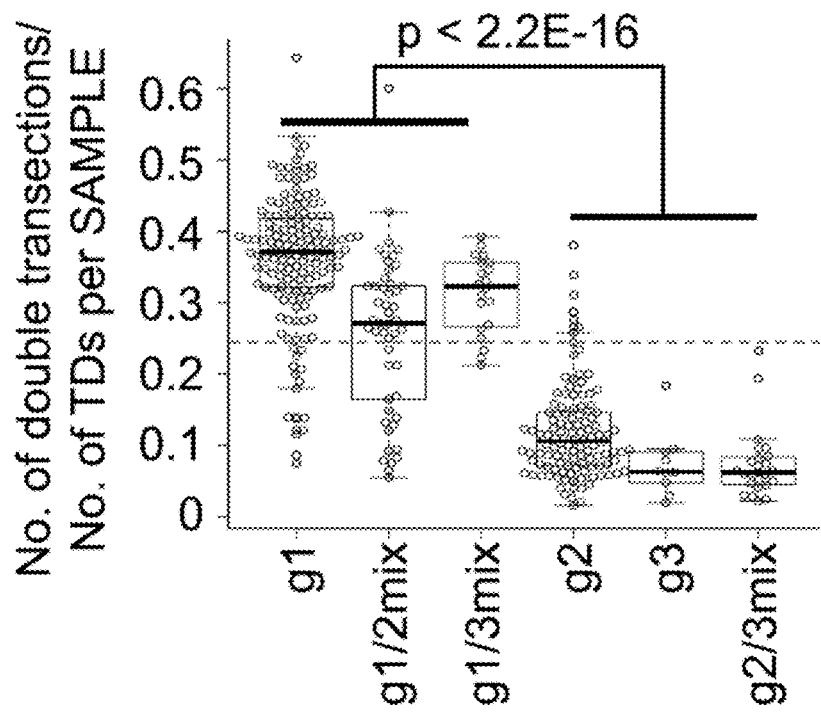
Figure 5C:
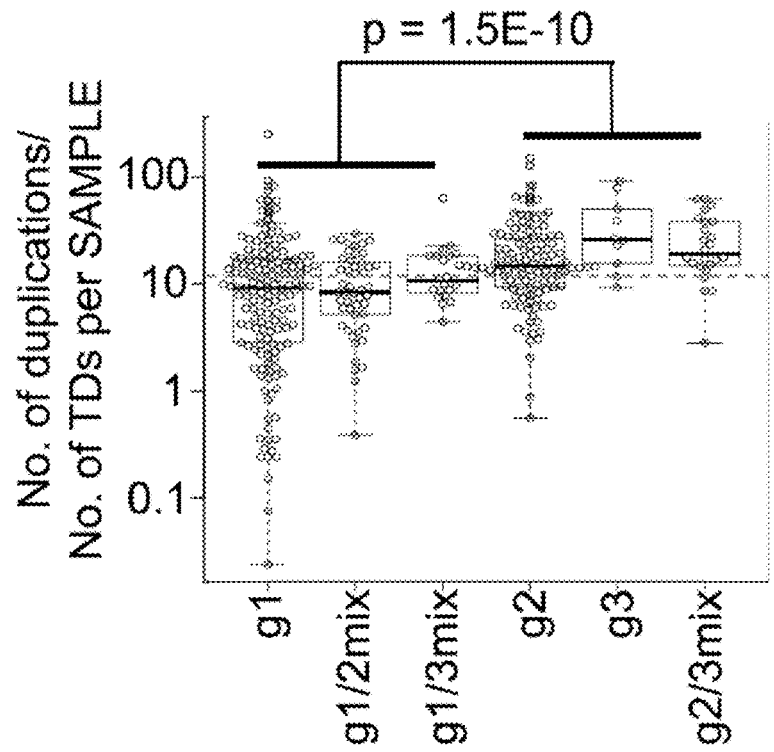

Example 6. Functional Consequences of TDPs: Gene Duplications and Gene Disruptions We have previously shown that TDs occurring in the context of TDP are more likely to affect gene bodies of oncogenes and TSGs than what is expected by chance alone, suggesting a strong selection for consequential genomic "scars" that favor oncogenesis (Menghi et al., 2016). Herein, we extended our analysis to account for the effect of TDs of different span sizes (class 1 versus class 2 versus class 3), occurring across the distinct TDP groups. A TD can affect gene body integrity in one of three ways: (1) the TD spans the entire length of a gene body resulting in gene duplication; (2) both TD breakpoints fall within the gene body resulting in a disruptive double transection; and (3) only one TD breakpoint falls within a target gene body, resulting in a de facto gene copy-number neutral rearrangement. We posited that these effects would be systematically mediated by TDs of different span sizes, with larger TDs (>231 kb, i.e., class 2 and class 3) being mostly involved in gene duplications and shorter TDs (_11 kb, i.e., class 1) more frequently causing gene disruptions via double transections. In fact, we observed that 45% of class 1 TDs (FIG. 5A) disrupt genes by double transection, but uncommonly result in single transections (18.2%) and even more rarely in gene duplications (5.7%), whereas the larger class 2 and class 3 TDs are more commonly implicated in single transections (66.9% and 74.7%, respectively) and in gene duplication (63.3% and 97.2%; FIG. 5A). Importantly, these observations suggest that, by virtue of the nature of the prevalent TDs in each TDP group, distinct TDP subgroups are subjected to different forms of gene perturbation. Indeed, we found that TDP tumors featuring a prominent class 1 TD modal peak (i.e., TDP groups 1, 1/2mix, and 1/3mix) share a larger number of gene disruptions due to double transections as opposed to the other TDP tumors (FIG. 5B). Conversely, TDP tumors with larger TD peaks (e.g., groups 2, 3, and 2/3mix) feature a significantly higher number of gene duplication events (FIG. 5C).

Figure 5D:
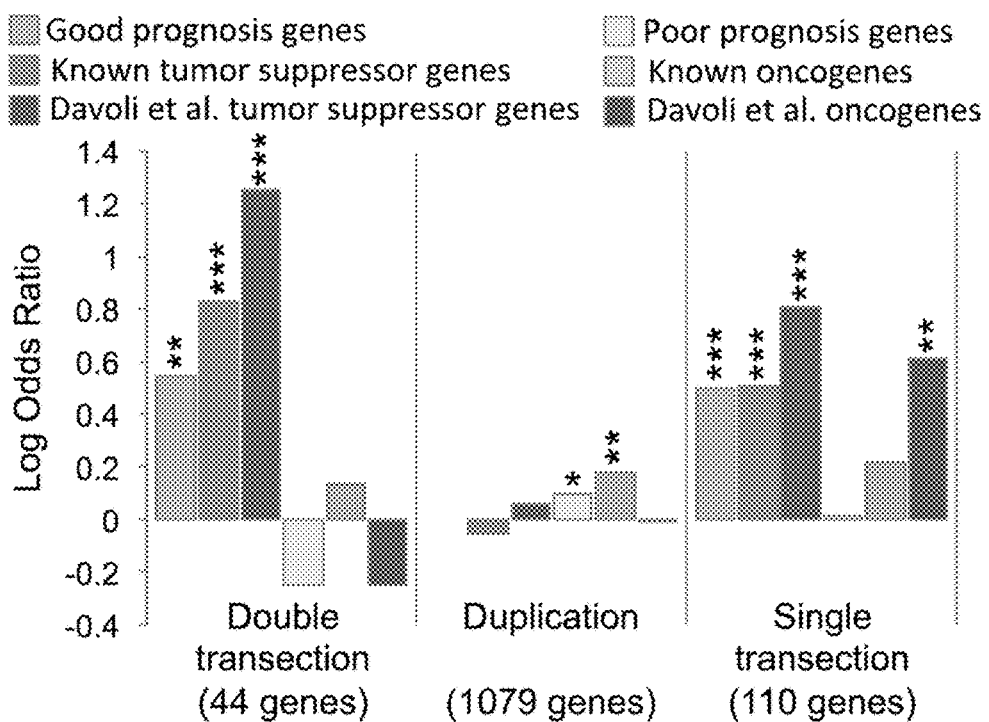
Figure 5E:
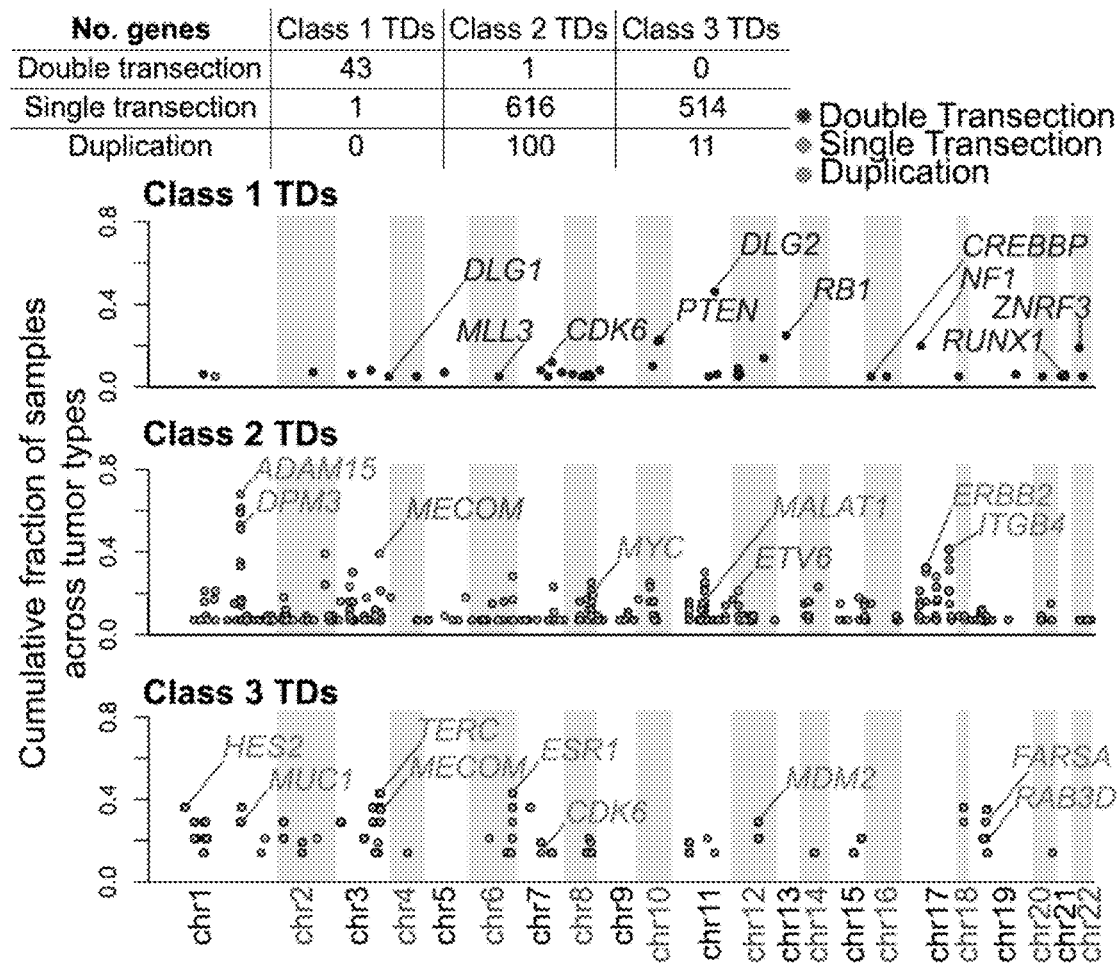

Given our observation that TSGs and oncogenes preferentially map to breakpoint hotspot regions associated with short (class 1) and larger (class 2) TDs, respectively, we predicted that these two classes of cancer genes would be directly altered by TDs in ways that augment oncogenicity. To test this hypothesis, we analyzed which types of genes are affected by TDs more frequently than expected by chance alone (see the Methods). We found that double transections, most commonly induced by class 1 TDs, predominantly and significantly disrupt TSGs, whereas gene duplications, which result from class 2 and class 3 TDs, predominantly engage oncogenes but not TSGs (FIGS. 5D and 5E). Genes undergoing single transections should theoretically result in functionally neutral events: one allele transected but compensated by the duplication in situ. However, there was primarily an enrichment of TSGs at the sites of the single transections (FIG. 5D). Though the precise mechanism is unclear, it is possible that the intact duplicated allele has been perturbed by either methylation, or by perturbation of specific regulatory elements, rendering the cell haplo-insufficient for the involved gene.

Figure 5F:
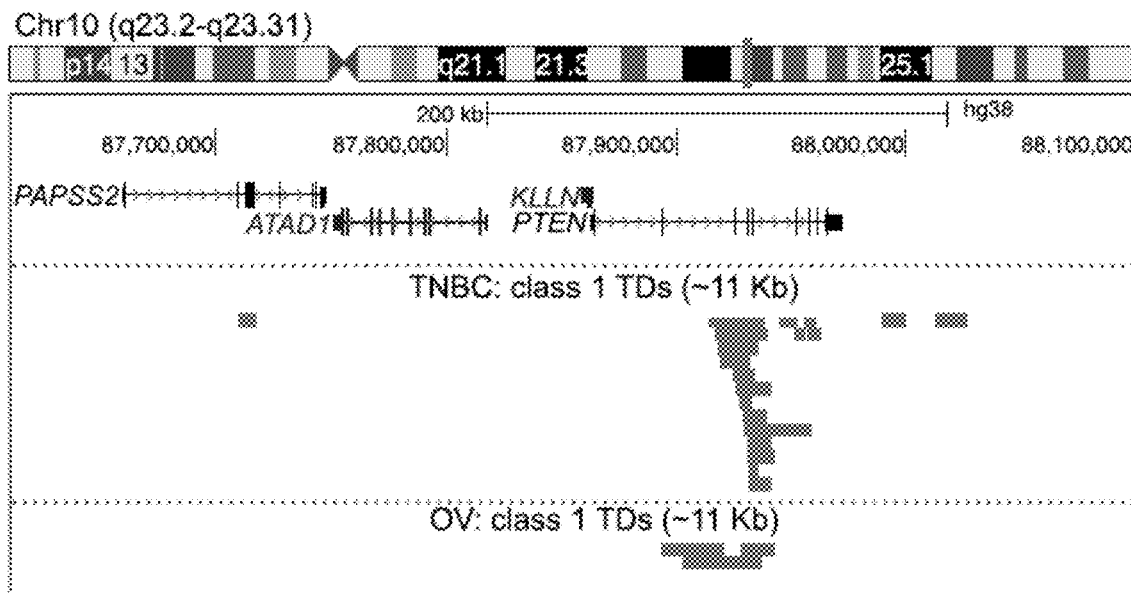
Figure 5G:
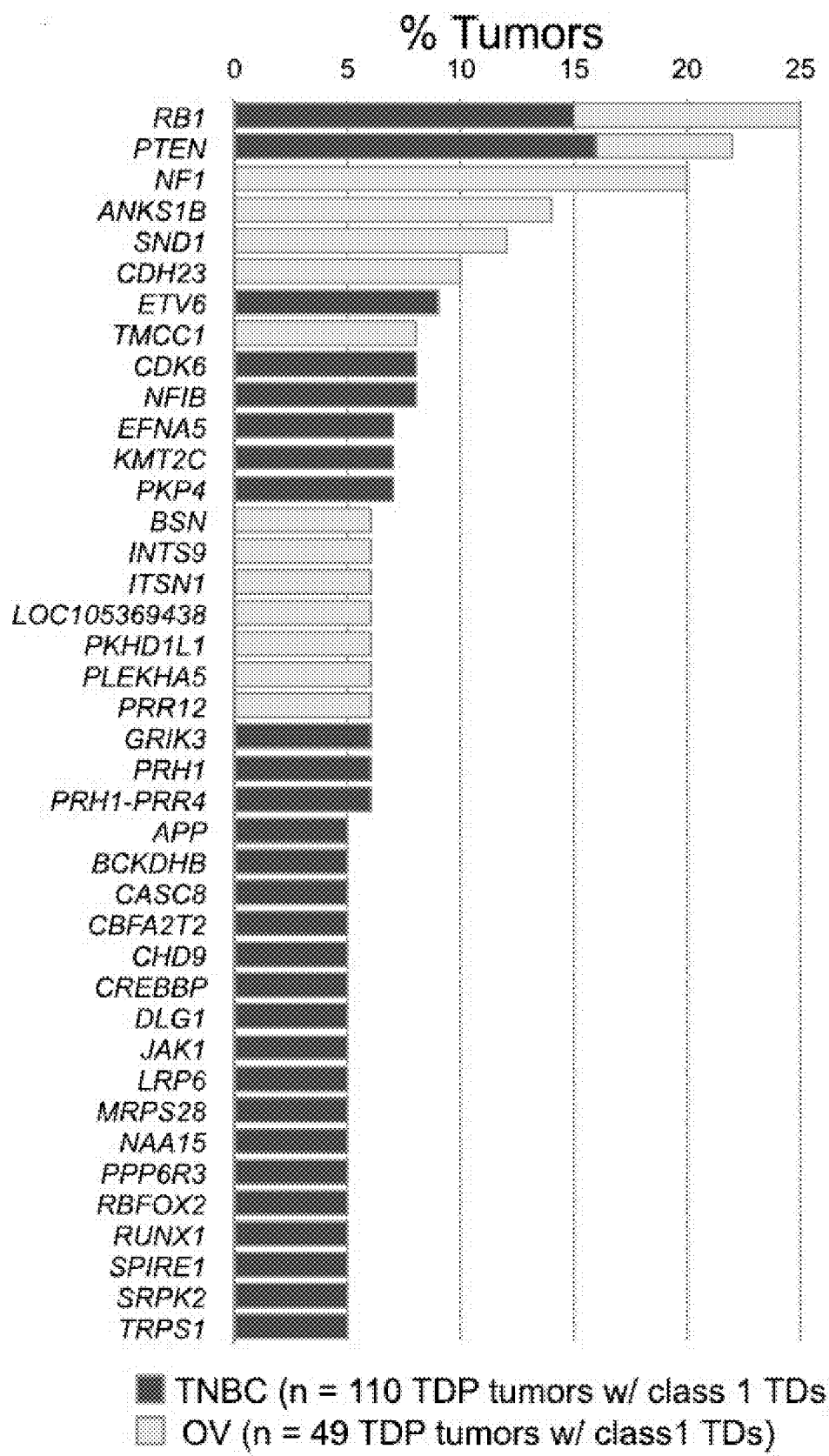

Among the most commonly disrupted TSGs were PTEN (affected in 16% and 6% of TNBC and OV TDPs with class 1 TDs), RB1 (15% and 10% of TNBC and OV TDPs class 1 TDs), and NF1 (20% of OV TDPs with class 1 TDs) (FIGS. 5E-5G). In the majority of the cases we examined, these highly recurrent and potentially oncogenic TD-mediated events appeared to occur independently from each other (data not shown). Of note, given the strong causality between loss of BRCA1 and the presence of class 1 TDs, a BRCA1-null status is also significantly associated with disruption of the PTEN, RB1, and NF1 genes via TD-mediated double transection in tumor samples that harbor wild-type exonic sequences for these genes (data not shown). This has implications for the clinical setting since this TD-mediated TSG disruption would not be detected using standard exome sequencing protocols (discussed below).

Genes that were recurrently duplicated by TDs included ERBB2 (duplicated in 16% of UCEC, 9% of TNBC, and 7% of OV TDPs with class 2 TDs), MYC (21% of TNBC TDPs with class 2 TDs), and ESR1 and MDM2 (36% and 29%, of OV TDPs class 3 TDs, respectively) (FIG. 5E). The oncogenic long non-coding RNA MALAT1 was also often subjected to duplication in TNBC TDP tumors with class 2 TDs (12%), suggesting its activation by gene duplication (data not shown).

Figure 6A:
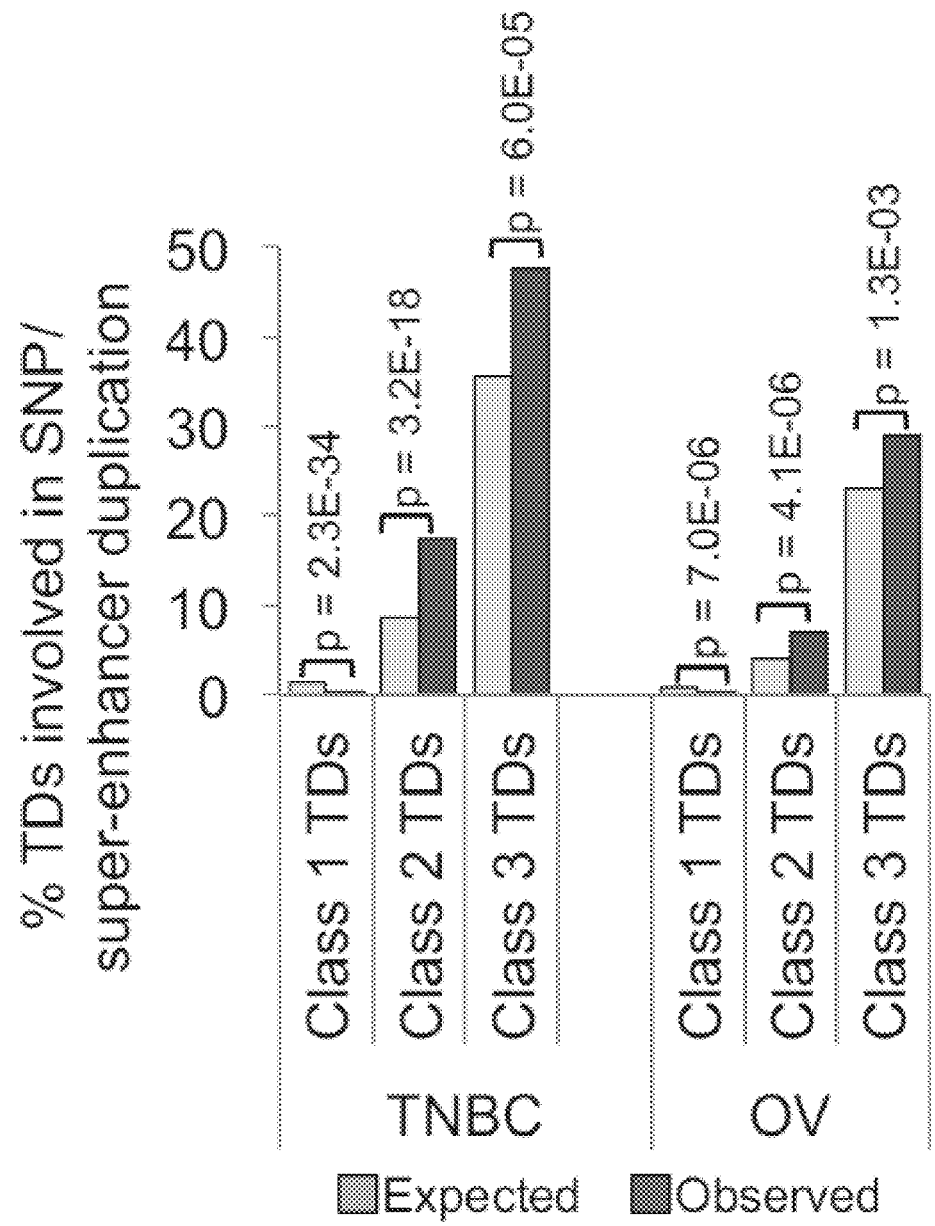
FIGS. 6A-6B. TD-Mediated Duplication of Tissue-Specific Regulatory Elements and TAD Boundaries in TDP Tumors.

Example 7. Functional Consequences of TDPs: Duplication of Regulatory Elements and of Chromatin Structures A recent study of breast cancer genomic rearrangements has found large span TDs (>100 kb) to frequently engage germline susceptibility loci and tissue-specific super-enhancers (Glodzik et al., 2017). Similarly, we found that cancer-associated SNPs identified by GWAS studies and tissue-specific super-enhancers are indeed commonly duplicated by large span TDs in TDP tumors. In TNBCs, both class 2 and class 3 TDs engage in the duplication of breast-specific regulatory elements more frequently than expected, based on 1,000 permutations of TD coordinates (FIG. 6A; data not shown). Conversely, class 1 TDs are significantly less frequently involved in the duplication of these regulatory elements, even when considering their differential sequence spans (FIG. 6A; data not shown).

Figure 6B:
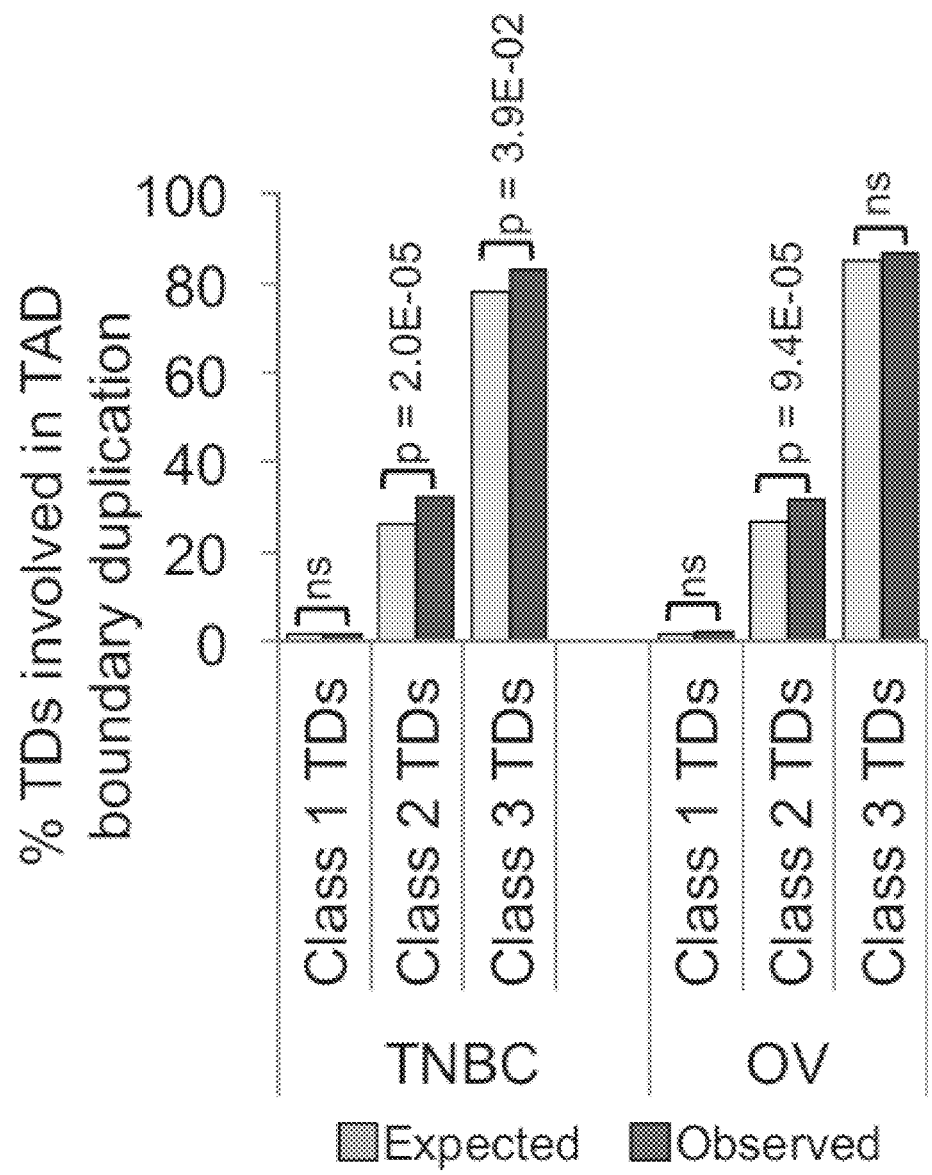

Topologically associating domains (TADs) are conserved 3D chromatin-folding arrangements in the genome that facilitate coordinated transcriptional regulation. Perturbations of TAD structures are associated with transcriptional remodeling and alterations in transcriptional control (Dixon et al., 2012). This is especially true when TAD boundaries are disrupted and alternative/illegitimate enhancers are allowed to engage target gene promoters. We assessed whether TAD boundaries are disrupted by TDs in TDP tumors. Specifically, we asked whether TAD boundaries are more likely to be duplicated by a TD in TNBC and, independently, in ovarian cancer. Using the CTCF-derived TAD genome map from the lymphoblastoid cell line GM12878 as reference (Tang et al., 2015), we mapped TD coordinates to the 3D genome. We found that TAD boundaries are statistically more frequently duplicated than expected by chance alone by class 2 TDs in both the TNBC and OV datasets (FIG. 6B; data not shown). By contrast only a very modest increase in TAD boundary duplications was seen for class 3 TDs in breast cancer, and no association at all was observed for class 1 TDs (FIG. 6B).

Figure 7A:
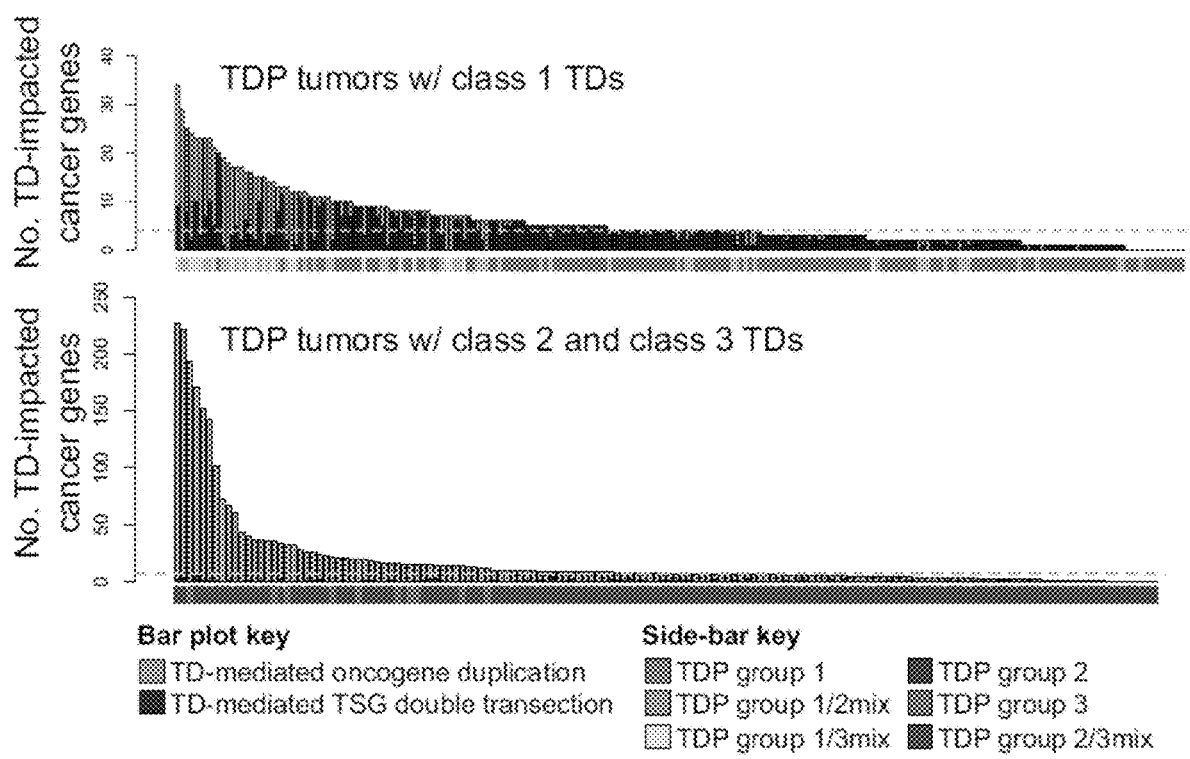
FIGS. 7A-7B. Number of TD-Mediated TSG Disruptions and Oncogene Duplications across Different TDP Groups.
Figure 7B:
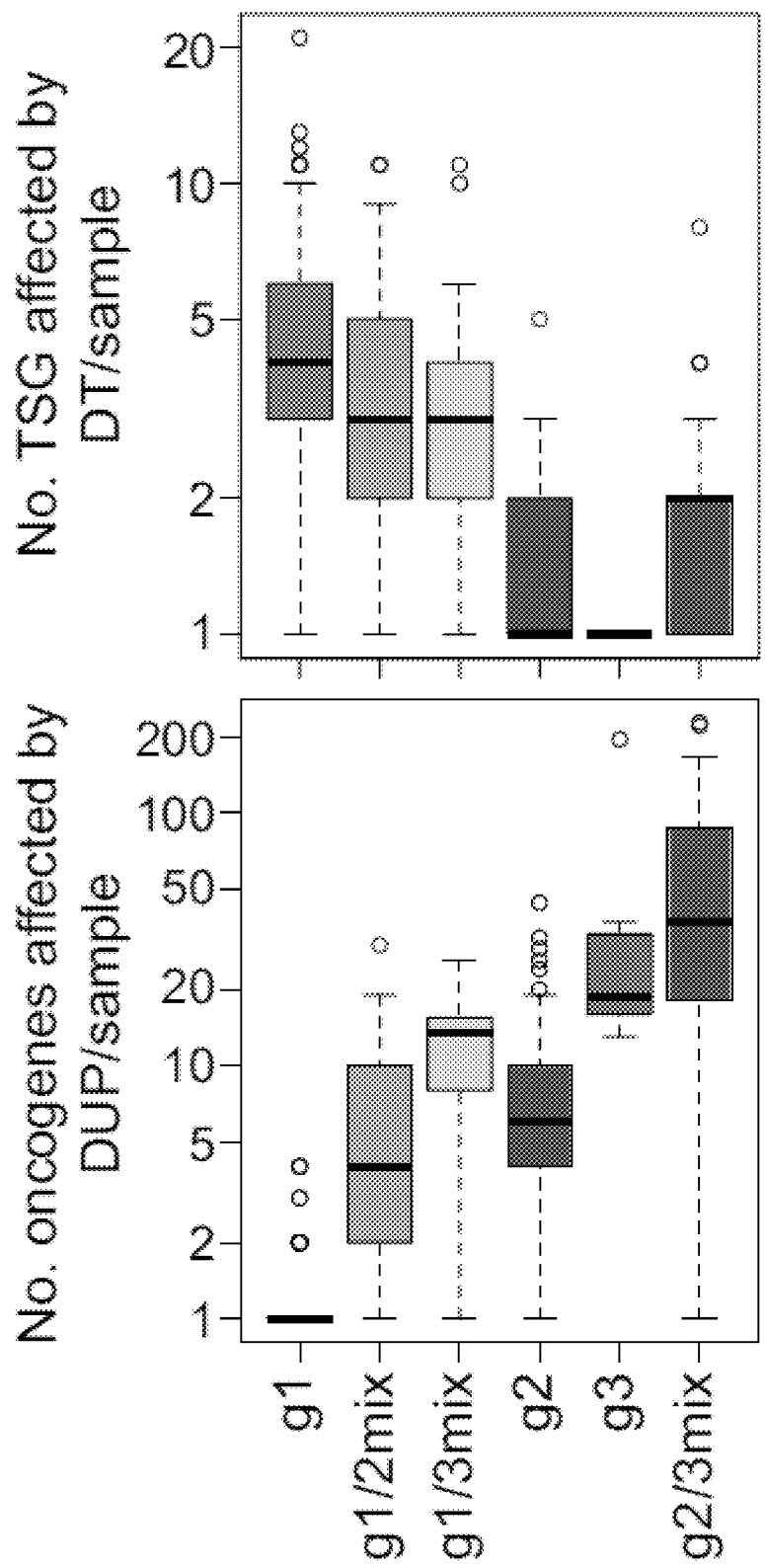

Taken together, these analyses show that TDs in the context of TDP target many known oncogenic elements rather than concentrating on a few recurrent genes. On average, class 1 TDs found in TDP group 1 tumors result in the disruption of 3.7 known TSGs per genome but do not engage in the duplication of other oncogenic elements (FIGS. 7A and 7B). TDP group 1/2mix and TDP group 1/3mix have on average 2.6 disrupted TSGs, and 5.6 and 11.8 duplicated oncogenes, respectively (FIGS. 7A and 7B). By contrast, TDP groups 2, 3, and 2/3mix tumors that only feature larger span TDs rarely feature double transection of TSGs (on average 0.4, 0, and 1 TSG is affected in TDP groups 2, 3, and 2/3mix, respectively), but they feature a higher number of duplications, with an average of 6.8, 37.4, and 63 duplicated oncogenes per cancer genome, respectively (FIGS. 7A and 7B).

EXPERIMENTAL MODEL AND SUBJECT DETAILS

PDXs

TNBC PDX models were established at The Jackson Laboratory campus, as previously described (Menghi et al., 2016). All animal procedures were approved by The Jackson Laboratory Institutional Animal Care and Use Committee (IACUC) under protocol number 12027.

Mouse Models of Breast Cancer

Mouse models of breast cancer were established in the Jos Jonkers lab, as previously described (Jonkers et al., 2001; Liu et al., 2007), in compliance with local and international regulations and ethical guidelines, and under authorization by the local animal experimental committee at the Netherlands Cancer Institute (DEC-NKI).

METHOD DETAILS

Data Collection for TDP Classification

A catalogue of somatic tandem duplications (TDs) in human cancer was compiled from a number of published studies and a variety of sources, including The Cancer Genome Atlas (TCGA), the International Cancer Genome Consortium (ICGC) and the Catalogue Of Somatic Mutations In Cancer (COSMIC). In cases where data from two or more tumor samples from the same patient donor was available, only one sample was selected for analysis. Priority was granted to primary tumors and tumors with the highest sequence coverage. In addition, 16 patient-derived xenograft (PDX) models of Triple Negative Breast Cancer (TNBC) were sequenced in-house. In total, 2717 tumor genomes from as many independent donors were assessed for the presence, genomic distribution and span size of somatic tandem duplications. The vast majority of the analyzed samples were primary solid tumors (n=2,451). The dataset also included 75 metastatic solid tumors, 8 solid tumor recurrences, 18 PDXs, 55 cell lines, 98 blood tumors and 12 ascites samples.

TCGA Cohort Data Collection and Processing

Whole Genome Sequencing (WGS) data for the 992 TCGA tumors analyzed in this study has been collected from the Cancer Genomics Hub (cghub.ucsc.edu/). Raw reads were aligned against the reference genome Hg19 and Speed-Seq (Chiang et al., 2015) was used to identify somatic rearrangements, as previously described (Barthel et al., 2017). Only tandem duplications with quality scores of 100 or greater and with both paired-end and split-read support were selected for TDP analysis, as these criteria have been reported to provide the highest confidence call set (Chiang et al., 2015).

Other Publicly Available WGS Cancer Cohorts

WGS-based somatic structural variation calls from three studies (Connor et al., 2017; Ferrari et al., 2016; Fujimoto et al., 2016) were downloaded from the ICGC Data Portal (dcc.icgc.org/) in November 2016 (data freeze version 22). WGS-based somatic structural variation calls from 13 other studies (Bailey et al., 2016; Bass et al., 2011; Berger et al., 2011; Campbell et al., 2010; Desmedt et al., 2015; Kataoka et al., 2015; Nik-Zainal et al., 2012, 2016; Northcott et al., 2012; Patch et al., 2015; Pinto et al., 2015; Stephens et al., 2009) were downloaded from the COSMIC data portal in September 2016 (data freeze version v78). Finally, WGS-based somatic structural variation calls from 13 additional independent studies were collected from the supplementary material of their corresponding publications (Baca et al., 2013; Berger et al., 2012; Grzeda et al., 2014; Hillmer et al., 2011; Imielinski et al., 2012; Inaki et al., 2014; McBride et al., 2012; Menghi et al., 2016; Natrajan et al., 2012; Ng et al., 2012; Popova et al., 2016; Totoki et al., 2014; Yang et al., 2013).

In-House WGS Cohort and Mouse Tumor Sequencing

The in-house WGS cohort consisted of 16 patient derived xenograft (PDX) TNBC models obtained from The Jackson Laboratory PDX inventory. Genomic libraries of 400 bp size were derived from the 16 PDX genomic DNA samples, using a KAPA Hyper Prep Kit according to manufacturer guidelines and 150 bp paired-end sequence reads were generated using the Illumina HiSeq X Ten system and aligned to the human genome (Hg19). Potential mouse contaminant reads were removed using Xenome (Conway et al., 2012). Structural variant calls were generated using four different tools (NBIC-seq (Xi et al., 2011), Crest (Wang et al., 2011), Delly (Rausch et al., 2012), and BreakDancer (Chen et al., 2009)), and high confidence events were selected when called by all four tools. In the absence of matched normal DNA samples to be used as controls, germline variants were identified as those that appear in the Database of Genomic Variants (DGV, dgv.tcag.ca/) and/or the 1,000 Genomes Project database (internationalgenome.org).

Mouse mammary tumors were generated in K14-cre; Trp53F/F (KP), WAP-cre;Trp53F/F (WP), K14-cre;Brca1F/F;Trp53F/F (KB1P), WAP-cre;Brca1F/F;Trp53F/F (WB1P), K14-cre;Brca2F/F;Trp53F/F (KB2P) and K14-cre;Brca1F/F; Brca2F/F;Trp53F/F (KB1B2P) female mice as described previously (Jonkers et al., 2001; Liu et al., 2007). Genomic libraries of 400 bp size were derived from 18 mouse tumor tissues and 2 mouse spleen tissues (normal controls) using a KAPA Hyper Prep Kit according to manufacturer guidelines. Mouse genomic libraries were sequenced using Illumina HiSeq 4000 to generate 150 bp paired-end sequence reads which were subsequently aligned to the mouse genome (Mm10). Structural variants were then predicted using a custom pipeline that combines the Hydra-Multi (Lindberg et al., 2015) and SpeedSeq (Chiang et al., 2015) algorithms. Structural variation data obtained from the two spleen DNA samples were used to remove germline variants.

The TDP Classification Algorithm

Step 1: Classification of the TCGA Cohort as the Test Set

A TDP score was computed for each tumor sample within the TCGA cohort (n=992) based on the number and chromosomal distribution of its somatic tandem duplications (TDs), as previously described (Menghi et al., 2016). Samples with no TDs but evidence of other types of somatic rearrangements and with a minimum sequence coverage of 6× were automatically scored as non-TDP.

For each one of the 118 tumors that featured a positive TDP score, we computed the span size density distribution of all the detected TDs. Using the turnpoints function of the pastecs R package, we identified the major peak of the distribution (i.e. mode) plus any additional peaks whose density measured at least 25% of the distribution mode. A total of 154 TD span size distribution peaks were identified across the 118 TDP TCGA tumors and they appeared to cluster along recurrent and clearly distinct span-size intervals (data not shown). To resolve the underlying distribution of the 154 identified TD span size distribution peaks, we used the Mclust function of the mclust R package and fit different numbers of mixture components (up to nine) to the peak distribution, using default estimates as the starting values for the iterative procedure. We compared the resulting mixture model estimates using the Bayesian information criterion and found that a mixture model comprising five Gaussian distributions with equal variance corresponded to the optimal fit. We then identified five non-overlapping span size intervals by setting thresholds corresponding to the intersections between each pair of adjacent Gaussian curves (<1.64 Kb, 1.64-51 Kb, 51-622 Kb, 622 Kb-6.2 Mb, >6.2 Mb) (data not shown). Based on these thresholds, we were able to classify each TD span size distribution peak as well as each individual TD into one of 5 span size classes (classes 0-4, data not shown).

Finally, we sub-grouped TDP tumors based on the presence of specific peaks/peak combinations, which appeared to be highly prevalent across the 118 TCGA TDP tumors. Tumors featuring a TD span size modal distribution were designated as TDP group 1, TDP group 2 and TDP group 3 based on the presence of a single TD span size distribution peak classified as class 1, class 2 and class 3, respectively. Similarly, tumors featuring a TD span size bimodal distribution were designated as TDP group 1/2mix (featuring class 1 and class 2 peaks), TDP group 1/3mix (featuring class 1 and class 3 peaks) and TDP group 2/3mix (featuring class 2 and class 3 peaks). Only one out of the 118 TDP tumors did not fit any of these profiles as it featured a class 0 peak and a class 4 peak but none of the class 1, class 2 or class 3 peaks. We labeled this tumor as unclassified and did not include it in any further analysis.

Step 2: Validation of the TDP Classification Algorithm on an Independent Collection of Sample Cohorts The TDP classification algorithm developed using the TCGA cohort as test set was applied to a completely independent dataset of 1725 tumor samples from individual patient donors, assembled from 30 different studies (referenced above) and representing 14 different tumor types. The algorithm performed consistently and robustly across the different studies of the validation cohort, by classifying 99% of the 258 TDP tumors in this cohort (257/258) into one of the six TDP subgroup profiles identified using the TCGA cohort, and by replicating similar frequencies of TDP subgroup occurrences within specific tumor types.

SNV Association Analysis

Somatic single nucleotide variation (SNV) data for the tumor samples analyzed in this study was downloaded in September 2016 from the COSMIC data portal (data freeze version v78). Only tumor samples classified as breast, ovarian or endometrial carcinomas and for which whole genome or whole exome sequencing data were available were considered for the SNV-TDP group association analysis (n=678). Only potentially damaging somatic variants were included in this analysis and comprised nonsense, frame-shift, splice site and missense mutations. Candidate genes associated with specific TDP states were considered those whose mutation rate was at least 10% and was specifically associated with only one distinct TDP profile and not any other, nor with non-TDP tumors. The significance of the associations was determined via Fisher's exact test. Given the large number of genes tested (n=17,332) and the relatively modest number of available samples for each TDP subgroup, none of the associations reached statistical significance after correcting for multiple testing. Nonetheless, non-corrected p values were utilized to rank genes and to identify the most likely candidates. Only two candidate genes emerged from this analysis (CDK12 in TDP group 2/3mix and FBXW7 in TDP group 2), and their association with the specific TDP subgroups was cross-validated by existing literature reports (CDK12 TD plus phenotype described by Popova et al. (Popova et al., 2016), in the case of CDK12) or alternative yet complementing gene mutations (CCNE1 amplification in the case of FBXW7).

CNV Association Analysis

The discovery phase of the copy number variant (CNV) association analysis was performed on the TCGA pan-cancer dataset, to allow for homogenously processed copy number information. Gene-based copy number calls relative to 977 tumor samples were obtained from the UCSC Cancer Genomic Browser (genome-cancer.ucsc.edu) (dataset ID: TCGA_PANCAN_gistic2, version: 2015-02-06). A liner mixed model (LMM) was used to identify the effect of TDP groups on copy number variations while controlling the variation from multiple tissues by including the tumor issue variable as random effect. Statistical analysis was performed using the package lmerTest (Kuznetsova et al., 2017) in R (version 3.3.0). P values were adjusted for multiple testing using Benjamini-Hochberg correction. Genes were then ranked based on the p value of their association with TDP group 2 relative to TDP group 1 and, independently, to non-TDP tumors. The top genes whose copy number change was associated with TDP group 2 tumors were identified as those with the highest cumulative rank.

Upon identification of the 19q12 amplicon as linked to TDP group 2 status, CNV data for the CCNE1 gene relative to the remaining tumor samples considered in this study was either retrieved from the COSMIC data portal (data freeze version v78) in the form of gene-based copy number value, or obtained from the supplementary material of the tumor samples' original publications, when available.

TD Breakpoint Analysis

Somatic TDs occurring across the entire pan-cancer dataset analyzed in this study (2717 tumor samples) were categorized into 4 classes as follows: (a) Class 1 TDs (_11 Kb) occurring in TDP tumors featuring a class 1 TD span size distribution peak (i.e. TDP groups 1, 1/2mix and 1/3mix; n=22,447 TDs); (b) Class 2 TDs (_231 Kb) from TDP tumors with a class 2 TD span size distribution peak (i.e., TDP groups 2, 1/2mix and 2/3mix; n=9794 TDs); (c) Class 3 TDs (_1.7 Mb) from TDP tumors with a class 3 TD span size distribution peak (i.e. TDP groups 3, 1/3mix and 2/3mix; n=2,586 TDs) and (d) Non-TDP TDs, i.e. all TDs occurring in non-TDP tumors, regardless of their individual span size (n=25,397 TDs). TD coordinates originally annotated using older genome assemblies were converted to the GRCh38/hg38 human genome version using the LiftOver tool of the UCSC Genome Browser (genome.ucsc.edu/index.html). All of the breakpoint coordinates relative to each TD class were then binned into consecutive, non-overlapping 500 Kb genomic windows. A TD breakpoint background distribution was generated by shuffling the TD coordinates 1,000 times. At each iteration, the genomic locations of the TDs were randomly permuted across the entire genome with the exclusion of centromeric and telomeric regions, while preserving TD numbers and span sizes. Genomic hotspots for TD breakpoints were identified as 500 Kb genomic windows with an observed number of breakpoints larger than the average count value obtained from the background distribution, plus standard deviations.

Analysis of Recurrently TD-Impacted Genes

TD-impacted genes were identified as those genes whose genomic location overlapped with that of one or more TDs. Every instance in which a gene and a TD featured some degree of genomic overlap was flagged as either (i) duplication (DUP), when the TD spanned the entire length of the gene body resulting in gene duplication; (ii) double transection (DT), when both TD breakpoints fell within the gene body resulting in the disruption of gene integrity or (iii) single transection (ST), when only one TD breakpoint fell within a target gene body, resulting in a de facto gene copy number neutral rearrangement. For each TD class and each tumor type examined, we computed the frequency with which any given gene appeared to be impacted in one of the three possible ways (i.e. DUP, DT or ST) and assigned empirical p values to these occurrences based on the number of times, out of 1,000 iterations, that a random permutation of the TD genomic locations would result in a similar or higher frequency. Recurrently TD-impacted genes were identified as those that appeared to be affected by TDs in any one of the three possible ways in at least 5% of the tumor samples examined and in a minimum of 3 tumor samples, and with a p value<0.05.

Cancer Gene Lists

Breast Cancer Survival Genes

Genes associated with breast cancer patients' prognosis data (good and poor prognosis genes) were identified as previously described (Inaki et al., 2014).

Known Cancer Genes

Lists of known tumor suppressor genes (TSGs) and oncogenes (OGs) were generated described before (Menghi et al., 2016).

Davoli Cancer Genes

Tumor suppressor genes (TSGs) and oncogenes (OGs) identified by Davoli et al. (Davoli et al., 2013).

Analysis of Disease-Associated Single Nucleotide Polymorphisms (SNPs) and Tissue-Specific Super-Enhancers Lists of tissue-specific super-enhancers and disease-associated SNPs relative to breast and ovarian tissues were obtained from Hnisz et al. (Hnisz et al., 2013). For both tumor types examined (TNBC and OV), and for each one of the 3 major classes of TDs occurring in TDP tumors, we computed the percentage of TDs that results in the duplication of SNPs and, separately, super-enhancers. The chi-squared test was used to compare the observed percentage to the expected one, computed as the mean value obtained from 1,000 random permutations of the TD genomic locations, as described above.

Analysis of Topologically Associating Domains (TADs)

Genomic coordinates relative to the full catalogue of TADs for the B lymphoblastoid cell line GM12878 were published before (Tang et al., 2015). For both tumor types examined (TNBC and OV), and for each one of the 3 major classes of TDs occurring in TDP tumors, we computed the percentage of TDs that overlap with TAD boundaries by at least one base pair. To compute the expected TD genomic distribution, genomic fragments were randomly sampled from non-centromere and non-telomere genomic region, with the requirement that the lengths of the sampled fragment fit the length distribution of the observed TDs. The randomly sampled fragments were then mapped to the TAD boundaries to calculate the expected percentage of TDs that overlap with TAD boundaries. The mean and standard deviation of the number of random fragments that overlap TAD boundaries were computed from 1,000 random permutations. The chi-squared test was used to compare the observed and expected values.

DATA AND SOFTWARE AVAILABILITY

WGS data relative to both the in-house sequenced cohort (i.e. 16 PDX TNBC models) and the mouse breast cancer models are available from the Sequence Read Archive database (ncbi.nlm.nih.gov/sra), SRA: PRJNA430898.

QUANTIFICATION AND STATISTICAL ANALYSIS

Unless otherwise stated, statistical analysis was performed and graphics produced using the R statistical programming language version 3.3.2 (cran.r-project.org). All hypothesis tests were two-sided when appropriate and the precise statistical tests employed are specified in Results and corresponding figure legends.

REFERENCES

Aladjem, M. I., Spike, B. T., Rodewald, L. W., Hope, T. J., Klemm, M., Jaenisch, R., and Wahl, G. M. (1998). ES cells do not activate p53-dependent stress responses and undergo p53-independent apoptosis in response to DNA damage. Curr. Biol. 8, 145-155.

Baca, S. C., Prandi, D., Lawrence, M. S., Mosquera, J. M., Romanel, A., Drier, Y., Park, K., Kitabayashi, N., MacDonald, T. Y., Ghandi, M., et al. (2013). Punctuated evolution of prostate cancer genomes. Cell 153, 666-677.

Bailey, P., Chang, D. K., Nones, K., Johns, A. L., Patch, A. M., Gingras, M. C., Miller, D. K., Christ, A. N., Bruxner, T. J., Quinn, M. C., et al. (2016). Genomic analyses identify molecular subtypes of pancreatic cancer. Nature 531, 47-52.

Barthel, F. P., Wei, W., Tang, M., Martinez-Ledesma, E., Hu, X., Amin, S. B., Akdemir, K. C., Seth, S., Song, X., Wang, Q., et al. (2017). Systematic analysis of telomere length and somatic alterations in 31 cancer types. Nat. Genet. 49, 349-357.

Bass, A. J., Lawrence, M. S., Brace, L. E., Ramos, A. H., Drier, Y., Cibulskis, K., Sougnez, C., Voet, D., Saksena, G., Sivachenko, A., et al. (2011). Genomic sequencing of colorectal adenocarcinomas identifies a recurrent VTI1ATCF7L2 fusion. Nat. Genet. 43, 964-968.

Berger, M. F., Hodis, E., Heffernan, T. P., Deribe, Y. L., Lawrence, M. S., Protopopov, A., Ivanova, E., Watson, L R., Nickerson, E., Ghosh, P., et al. (2012). Melanoma genome sequencing reveals frequent PREX2 mutations. Nature 485, 502-506.

Berger, M. F., Lawrence, M. S., Demichelis, F., Drier, Y., Cibulskis, K., Sivachenko, A. Y., Sboner, A., Esgueva, R., Pflueger, D., Sougnez, C., et al. (2011). The genomic complexity of primary human prostate cancer. Nature 470, 214-220.

Bester, A. C., Roniger, M., Oren, Y. S., Im, M. M., Sarni, D., Chaoat, M., Bensimon, A., Zamir, G., Shewach, D. S., and Kerem, B. (2011). Nucleotide deficiency promotes genomic instability in early stages of cancer development. Cell 145, 435-446.

Blazek, D., Kohoutek, J., Bartholomeeusen, K., Johansen, E., Hulinkova, P., Luo, Z., Cimermancic, P., Ule, J., and Peterlin, B. M. (2011). The cyclin K/Cdk12 complex maintains genomic stability via regulation of expression of DNA damage response genes. Genes Dev. 25, 2158-2172.

Campbell, P. J., Yachida, S., Mudie, L. J., Stephens, P. J., Pleasance, E. D., Stebbings, L. A., Morsberger, L. A., Latimer, C., McLaren, S., Lin, M. L., et al. (2010). The patterns and dynamics of genomic instability in metastatic pancreatic cancer. Nature 467, 1109-1113.

Cancer Genome Atlas Research Network, Kandoth, C., Schultz, N., Cherniack, A. D., Akbani, R., Liu, Y., Shen, H., Robertson, A. G., Pashtan, I., Shen, R., Benz, C. C., et al. (2013). Integrated genomic characterization of endometrial carcinoma. Nature 497, 67-73.

Chen, K., Wallis, J. W., McLellan, M. D., Larson, D. E., Kalicki, J. M., Pohl, C. S., McGrath, S. D., Wendl, M. C., Zhang, Q., Locke, D. P., et al. (2009). BreakDancer: an algorithm for high-resolution mapping of genomic structural variation. Nat. Methods 6, 677-681.

Chiang, C., Layer, R. M., Faust, G. G., Lindberg, M. R., Rose, D. B., Garrison, E. P., Marth, G. T., Quinlan, A. R., and Hall, I. M. (2015). SpeedSeq: ultra-fast personal genome analysis and interpretation. Nat. Methods 12, 966-968. Connor, A. A., Denroche, R. E., Jang, G. H., Timms, L., Kalimuthu, S. N., Selander, I., McPherson, T., Wilson, G. W., Chan-Seng-Yue, M. A., Borozan, I., et al. (2017). Association of distinct mutational signatures with correlates of increased immune activity in pancreatic ductal adenocarcinoma. JAMA Oncol. 3, 774-783.

Conway, T., Wazny, J., Bromage, A., Tymms, M., Sooraj, D., Williams, E. D., and Beresford-Smith, B. (2012). Xenome—a tool for classifying reads from xenograft samples. Bioinformatics 28, i172-i178.

Cook, R., Zoumpoulidou, G., Luczynski, M. T., Rieger, S., Moquet, J., Spanswick, V. J., Hartley, J. A., Rothkamm, K., Huang, P. H., and Mittnacht, S. (2015). Direct involvement of retinoblastoma family proteins in DNA repair by non-homologous end-joining. Cell Rep. 10, 2006-2018.

Costantino, L., Sotiriou, S. K., Rantala, J. K., Magin, S., Mladenov, E., Helleday, T., Haber, J. E., Iliakis, G., Kallioniemi, O. P., and Halazonetis, T. D. (2014). Break-induced replication repair of damaged forks induces genomic duplications in human cells. Science 343, 88-91.

Davoli, T., Xu, A. W., Mengwasser, K. E., Sack, L. M., Yoon, J. C., Park, P. J., and Elledge, S. J. (2013). Cumulative haploinsufficiency and triplosensitivity drive aneuploidy patterns and shape the cancer genome. Cell 155, 948-962.

Desmedt, C., Fumagalli, D., Pietri, E., Zoppoli, G., Brown, D., Nik-Zainal, S., Gundem, G., Rothe, F., Majjaj, S., Garuti, A., et al. (2015). Uncovering the genomic heterogeneity of multifocal breast cancer. J. Pathol. 236, 457-466.

Dixon, J. R., Selvaraj, S., Yue, F., Kim, A., Li, Y., Shen, Y., Hu, M., Liu, J. S., and Ren, B. (2012). Topological domains in mammalian genomes identified by analysis of chromatin interactions. Nature 485, 376-380.

Etemadmoghadam, D., Weir, B. A., Au-Yeung, G., Alsop, K., Mitchell, G., George, J., Australian Ovarian Cancer Study, G., Davis, S., D'Andrea, A. D., Simpson, K., et al. (2013). Synthetic lethality between CCNE1 amplification and loss of BRCA1. Proc. Natl. Acad. Sci. USA 110, 19489-19494.

Ferrari, A., Vincent-Salomon, A., Pivot, X., Sertier, A. S., Thomas, E., Tonon, L., Boyault, S., Mulugeta, E., Treilleux, I., MacGrogan, G., et al. (2016). A whole genome sequence and transcriptome perspective on HER2-positive breast cancers. Nat. Commun. 7, 12222.

Fujimoto, A., Furuta, M., Totoki, Y., Tsunoda, T., Kato, M., Shiraishi, Y., Tanaka, H., Taniguchi, H., Kawakami, Y., Ueno, M., et al. (2016). Whole-genome mutational landscape and characterization of noncoding and structural mutations in liver cancer. Nat. Genet. 48, 500-509.

Glodzik, D., Morganella, S., Davies, H., Simpson, P. T., Li, Y., Zou, X., Diez-Perez, J., Staaf, J., Alexandrov, L. B., Smid, M., et al. (2017). A somaticmutational process recurrently duplicates germline susceptibility loci and tissue-specific super-enhancers in breast cancers. Nat. Genet. 49, 341-348.

Grzeda, K. R., Royer-Bertrand, B., Inaki, K., Kim, H., Hillmer, A. M., Liu, E. T., and Chuang, J. H. (2014). Functional chromatin features are associated with structural mutations in cancer. BMC Genomics 15, 1013.

He, J., Kang, X., Yin, Y., Chao, K. S., and Shen, W. H. (2015). PTEN regulates DNA replication progression and stalled fork recovery. Nat. Commun. 6, 7620.

Hillmer, A. M., Yao, F., Inaki, K., Lee, W. H., Ariyaratne, P. N., Teo, A. S., Woo, X. Y., Zhang, Z., Zhao, H., Ukil, L., et al. (2011). Comprehensive long-span paired-end-tag mapping reveals characteristic patterns of structural variations in epithelial cancer genomes. Genome Res. 21, 665-675.

Hnisz, D., Abraham, B. J., Lee, T. I., Lau, A., Saint-Andre, V., Sigova, A. A., Hoke, H. A., and Young, R. A. (2013). super-enhancers in the control of cell identity and disease. Cell 155, 934-947.

Imielinski, M., Berger, A. H., Hammerman, P. S., Hernandez, B., Pugh, T. J., Hodis, E., Cho, J., Suh, J., Capelletti, M., Sivachenko, A., et al. (2012). Mapping the hallmarks of lung adenocarcinoma with massively parallel sequencing. Cell 150, 1107-1120.

Inaki, K., Menghi, F., Woo, X. Y., Wagner, J. P., Jacques, P. E., Lee, Y. F., Shreckengast, P. T., Soon, W. W., Malhotra, A., Teo, A. S., et al. (2014). Systems consequences of amplicon formation in human breast cancer. Genome Res. 24, 1559-1571.

Jonkers, J., Meuwissen, R., van der Gulden, H., Peterse, H., van der Valk, M., and Berns, A. (2001). Synergistic tumor suppressor activity of BRCA2 and p53 in a conditional mouse model for breast cancer. Nat. Genet. 29, 418-425.

Joshi, P. M., Sutor, S. L., Huntoon, C. J., and Karnitz, L. M. (2014). Ovarian cancer-associated mutations disable catalytic activity of CDK12, a kinase that promotes homologous recombination repair and resistance to cisplatin and poly(ADP-ribose) polymerase inhibitors. J. Biol. Chem. 289, 9247-9253.

Kataoka, K., Nagata, Y., Kitanaka, A., Shiraishi, Y., Shimamura, T., Yasunaga, J., Totoki, Y., Chiba, K., Sato-Otsubo, A., Nagae, G., et al. (2015). Integrated molecular analysis of adult T cell leukemia/lymphoma. Nat. Genet. 47, 1304-1315.

Klotz, K., Cepeda, D., Tan, Y., Sun, D., Sangfelt, O., and Spruck, C. (2009). SCF(Fbxw7/hCdc4) targets cyclin E2 for ubiquitin-dependent proteolysis. Exp. Cell Res. 315, 1832-1839.

Kuznetsova, A., Brockhoff, P. B., and Christensen, R. H. B. (2017). lmerTest package: tests in linear mixed effects models. J. Stat. Softw. 82, 1-26.

Lindberg, M. R., Hall, I. M., and Quinlan, A. R. (2015). Population-based structural variation discovery with Hydra-Multi. Bioinformatics 31, 1286-1289.

Liu, X., Holstege, H., van der Gulden, H., Treur-Mulder, M., Zevenhoven, J., Velds, A., Kerkhoven, R. M., van Vliet, M. H., Wessels, L. F., Peterse, J. L., et al. (2007). Somatic loss of BRCA1 and p53 in mice induces mammary tumors with features of human BRCA1-mutated basal-like breast cancer. Proc. Natl. Acad. Sci. USA 104, 12111-12116.

McBride, D. J., Etemadmoghadam, D., Cooke, S. L., Alsop, K., George, J., Butler, A., Cho, J., Galappaththige, D., Greenman, C., Howarth, K. D., et al. (2012). Tandem duplication of chromosomal segments is common in ovarian and breast cancer genomes. J. Pathol. 227, 446-455.

Mendes-Pereira, A. M., Martin, S. A., Brough, R., McCarthy, A., Taylor, J. R., Kim, J. S., Waldman, T., Lord, C. J., and Ashworth, A. (2009). Synthetic lethal targeting of PTEN mutant cells with PARP inhibitors. EMBO Mol. Med. 1, 315-322.

Menghi, F., Inaki, K., Woo, X., Kumar, P. A., Grzeda, K. R., Malhotra, A., Yadav, V., Kim, H., Marquez, E. J., Ucar, D., et al. (2016). The tandem duplicator phenotype as a distinct genomic configuration in cancer. Proc. Natl. Acad. Sci. USA 113, E2373-E2382.

Menghi, F., and Liu, E. T. (2016). Reply to Watkins et al.: whole-genome sequencing-based identification of diverse tandem duplicator phenotypes in human cancers. Proc. Natl. Acad. Sci. USA 113, E5259-E5260.

Natrajan, R., Mackay, A., Lambros, M. B., Weigelt, B., Wilkerson, P. M., Manie, E., Grigoriadis, A., A'Hern, R., van der Groep, P., Kozarewa, I., et al. (2012). A whole-genome massively parallel sequencing analysis of BRCA1 mutant oestrogen receptor-negative and -positive breast cancers. J. Pathol. 227, 29-41.

Ng, C. K., Cooke, S. L., Howe, K., Newman, S., Xian, J., Temple, J., Batty, E. M., Pole, J. C., Langdon, S. P., Edwards, P. A., and Brenton, J. D. (2012). The role of tandem duplicator phenotype in tumour evolution in high-grade serous ovarian cancer. J. Pathol. 226, 703-712.

Nik-Zainal, S., Alexandrov, L. B., Wedge, D. C., Van Loo, P., Greenman, C. D., Raine, K., Jones, D., Hinton, J., Marshall, J., Stebbings, L. A., et al. (2012). Mutational processes molding the genomes of 21 breast cancers. Cell 149, 979-993.

Nik-Zainal, S., Davies, H., Staaf, J., Ramakrishna, M., Glodzik, D., Zou, X., Martincorena, I., Alexandrov, L. B., Martin, S., Wedge, D. C., et al. (2016). Landscape of somatic mutations in 560 breast cancer whole-genome sequences. Nature 534, 47-54.

Northcott, P. A., Shih, D. J., Peacock, J., Garzia, L., Morrissy, A. S., Zichner, T., Stutz, A. M., Korshunov, A., Reimand, J., Schumacher, S. E., et al. (2012). Subgroup-specific structural variation across 1,000 medulloblastoma genomes. Nature 488, 49-56.

Patch, A. M., Christie, E. L., Etemadmoghadam, D., Garsed, D. W., George, J., Fereday, S., Nones, K., Cowin, P., Alsop, K., Bailey, P. J., et al. (2015). Whole-genome characterization of chemoresistant ovarian cancer. Nature 521, 489-494.

Pathania, S., Nguyen, J., Hill, S. J., Scully, R., Adelmant, G. O., Marto, J. A., Feunteun, J., and Livingston, D. M. (2011). BRCA1 is required for postreplication repair after UV-induced DNA damage. Mol. Cell 44, 235-251.

Pinto, E. M., Chen, X., Easton, J., Finkelstein, D., Liu, Z., Pounds, S., Rodriguez-Galindo, C., Lund, T. C., Mardis, E. R., Wilson, R. K., et al. (2015). Genomic landscape of paediatric adrenocortical tumours. Nat. Commun. 6, 6302.

Popova, T., Manie, E., Boeva, V., Battistella, A., Goundiam, O., Smith, N. K., Mueller, C. R., Raynal, V., Mariani, O., Sastre-Garau, X., and Stern, M. H. (2016). Ovarian cancers harboring inactivating mutations in CDK12 display a distinct genomic instability pattern characterized by large tandem duplications. Cancer Res. 76, 1882-1891.

Prakash, R., Zhang, Y., Feng, W., and Jasin, M. (2015). Homologous recombination and human health: the roles of BRCA1, BRCA2, and associated proteins. Cold Spring Harb. Perspect. Biol. 7, a016600.

Rausch, T., Zichner, T., Schlattl, A., Stutz, A. M., Benes, V., and Korbel, J. O. 0(2012). DELLY: structural variant discovery by integrated paired-end and split-read analysis. Bioinformatics 28, i333-i339.

Schlacher, K., Wu, H., and Jasin, M. (2012). A distinct replication fork protection pathway connects Fanconi anemia tumor suppressors to RAD51-BRCA1/2. Cancer Cell 22, 106-116.

Shen, W. H., Balajee, A. S., Wang, J., Wu, H., Eng, C., Pandolfi, P. P., and Yin, Y. (2007). Essential role for nuclear PTEN in maintaining chromosomal integrity. Cell 128, 157-170.

Stephens, P. J., Greenman, C. D., Fu, B., Yang, F., Bignell, G. R., Mudie, L. J., Pleasance, E. D., Lau, K. W., Beare, D., Stebbings, L. A., et al. (2011). Massive genomic rearrangement acquired in a single catastrophic event during cancer development. Cell 144, 27-40.

Stephens, P. J., McBride, D. J., Lin, M. L., Varela, I., Pleasance, E. D., Simpson, J. T., Stebbings, L. A., Leroy, C., Edkins, S., Mudie, L. J., et al. (2009). Complex landscapes of somatic rearrangement in human breast cancer genomes. Nature 462, 1005-1010.

Tang, Z., Luo, O. J., Li, X., Zheng, M., Zhu, J. J., Szalaj, P., Trzaskoma, P., Magalska, A., Wlodarczyk, J., Ruszczycki, B., et al. (2015). CTCF-mediated human 3D genome architecture reveals chromatin topology for transcription. Cell 163, 1611-1627.

Teixeira, L. K., Wang, X., Li, Y., Ekholm-Reed, S., Wu, X., Wang, P., and Reed, S. I. (2015). Cyclin E deregulation promotes loss of specific genomic regions. Curr. Biol. 25, 1327-1333.

Totoki, Y., Yoshida, A., Hosoda, F., Nakamura, H., Hama, N., Ogura, K., Yoshida, A., Fujiwara, T., Arai, Y., Toguchida, J., et al. (2014). Unique mutation portraits and frequent COL2A1 gene alteration in chondrosarcoma. Genome Res. 24, 1411-1420.

Wallace, M. D., Pfefferle, A. D., Shen, L., McNairn, A. J., Cerami, E. G., Fallon, B. L., Rinaldi, V. D., Southard, T. L., Perou, C. M., and Schimenti, J. C. (2012). Comparative oncogenomics implicates the neurofibromin 1 gene (NF1) as a breast cancer driver. Genetics 192, 385-396.

Wang, J., Mullighan, C. G., Easton, J., Roberts, S., Heatley, S. L., Ma, J., Rusch, M. C., Chen, K., Harris, C. C., Ding, L., et al. (2011). CREST maps somatic structural variation in cancer genomes with base-pair resolution. Nat. Methods 8, 652-654.

Willis, N. A., Frock, R. L., Menghi, F., Duffey, E. E., Panday, A., Camacho, V., Hasty, E. P., Liu, E. T., Alt, F. W., and Scully, R. (2017). Mechanism of tandem duplication formation in BRCA1-mutant cells. Nature 551, 590-595.

Xi, R., Hadjipanayis, A. G., Luquette, L. J., Kim, T. M., Lee, E., Zhang, J., 0Johnson, M. D., Muzny, D. M., Wheeler, D. A., Gibbs, R. A., et al. (2011). Copy number variation detection in whole-genome sequencing data using the Bayesian information criterion. Proc. Natl. Acad. Sci. USA 108, E1128-E1136.

Yang, L., Luquette, L. J., Gehlenborg, N., Xi, R., Haseley, P. S., Hsieh, C. H., Zhang, C., Ren, X., Protopopov, A., Chin, L., et al. (2013). Diverse mechanisms of somatic structural variations in human cancer genomes. Cell 153, 919-929.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "about" and "substantially" preceding a numerical value mean±10% of the recited numerical value.

Where a range of values is provided, each value between the upper and lower ends of the range are specifically contemplated and described herein.

What is claimed is:

1. A method, comprising:
   (a) calculating a tandem duplicator phenotype (TDP) score for a genome of a tumor sample obtained from a subject,
   wherein the TDP score is calculated using the following equation:

$$TDP\ score = -\frac{\sum_i |Obs_i - Exp_i|}{TD} + k$$

wherein tandem duplication (TD) is the total number of tandem duplications in the tumor sample, $Obs_i$ is the observed number of tandem duplications for each chromosome i in the genome, $Exp_i$ is the expected number of tandem duplications for each chromosome i in the genome, and k is 0.71;
   (b) measuring a length distribution of tandem duplications in the tumor sample with a TDP score above a threshold value of zero (0);
   (c) assigning to the tumor sample one of at least six TDP subtypes based on the length distribution of the tandem duplications, wherein the tumor sample is assigned a Group 1 TDP subtype, a Group 1/2mix TDP subtype, or a Group 1/3mix TDP subtype;
   (d) identifying the subject as a candidate for a therapy that targets tumors comprising tandem duplications in PTEN, RB1, and/or NF1 based on the TDP subtype of the tumor sample; and
   (e) administering to the subject a therapy that comprises a platinum-based agent and/or an alkylating agent.

2. The method of claim 1, wherein the at least six TDP subtypes are selected from the group consisting of: Group 1 TDP subtype, Group 2 TDP subtype, Group 3 TDP subtype, Group 1/2mix TDP subtype, Group 1/3mix TDP subtype, and Group 2/3mix TDP subtype.

3. The method of claim 2, wherein the Group 1 TDP subtype is assigned to a tumor sample that comprises tandem duplications having a length of about 11 kb, the Group 2 TDP subtype is assigned to a tumor sample that comprises tandem duplications having a length of about 231 kb, the Group 3 TDP subtype is assigned to a tumor sample that comprises tandem duplications having a length of about 1.7 Mb, the Group 1/2mix TDP subtype is assigned to a tumor sample that comprises tandem duplications having a length of about 11 kb and tandem duplications having a length of about 231 kb, the Group 1/3mix TDP subtype is assigned to a tumor sample that comprises tandem duplications having a length of about 11 kb and tandem duplications having a length of about 1.7 Mb, and the Group 2/3mix TDP subtype is assigned to a tumor sample that comprises tandem duplications having a length of about 231 kb and tandem duplications having a length of about 1.7 Mb.

4. The method of claim 1, wherein the therapy modulates BRCA1 and/or p53 activity.

\* \* \* \* \*